(12) United States Patent
Yamamori et al.

(10) Patent No.: US 8,053,445 B2
(45) Date of Patent: Nov. 8, 2011

(54) UTILITIES OF OLEFIN DERIVATIVES

(75) Inventors: Teruo Yamamori, Takarazuka (JP); Kiyoshi Nagata, Osaka (JP); Kunio Hayashi, Kadoma (JP)

(73) Assignee: Shionogi & Co., Ltd., Osaka (JP)

( * ) Notice: Subject to any disclaimer, the term of this patent is extended or adjusted under 35 U.S.C. 154(b) by 7 days.

(21) Appl. No.: 12/230,993

(22) Filed: Sep. 9, 2008

(65) Prior Publication Data
US 2009/0036457 A1 Feb. 5, 2009

Related U.S. Application Data

(62) Division of application No. 10/489,365, filed as application No. PCT/JP01/07981 on Sep. 14, 2001.

(51) Int. Cl.
*A61K 31/47* (2006.01)
(52) U.S. Cl. ....................................... 514/311
(58) Field of Classification Search ................... 514/311
See application file for complete search history.

(56) References Cited

U.S. PATENT DOCUMENTS

| | | | |
|---|---|---|---|
| 4,714,762 A | 12/1987 | Hoefle et al. | |
| 5,234,946 A | 8/1993 | Takezawa et al. | |
| 5,389,666 A | 2/1995 | Hamanaka et al. | |
| 5,409,930 A | 4/1995 | Spada et al. | |
| 5,621,010 A | 4/1997 | Sueda et al. | |
| 5,643,932 A | 7/1997 | Chihiro et al. | |
| 5,700,823 A | 12/1997 | Hirth et al. | |
| 5,874,431 A * | 2/1999 | Stevens et al. | 514/233.8 |
| 5,919,970 A | 7/1999 | Song et al. | |
| 6,120,994 A | 9/2000 | Tam | |
| 2004/0235877 A1* | 11/2004 | Ishizuka et al. | 514/277 |
| 2004/0248950 A1* | 12/2004 | Ishizuka et al. | 514/363 |
| 2007/0190041 A1* | 8/2007 | Sasahara et al. | 424/94.5 |

FOREIGN PATENT DOCUMENTS

| | | |
|---|---|---|
| EP | 0 528 146 | 2/1993 |
| EP | 0 718 285 | 6/1996 |
| JP | 1-175965 | 7/1989 |
| JP | 3-34967 | 2/1991 |
| JP | 3-173865 | 7/1991 |
| JP | 3-193746 | 8/1991 |
| JP | 4-50930 | 2/1992 |
| JP | 4-66571 | 3/1992 |
| JP | 5-51318 | 3/1993 |
| JP | 6-507643 | 9/1994 |
| JP | 7-145057 | 6/1995 |
| JP | 7-258200 | 10/1995 |
| JP | 2001-97979 | 4/2001 |
| JP | 2001-131151 | 5/2001 |
| JP | 2001131151 A * | 5/2001 |
| JP | 2001-233767 | 8/2001 |
| WO | 96/39387 | 12/1996 |
| WO | 97/09048 | 3/1997 |
| WO | 97/32574 | 9/1997 |
| WO | 98/14431 | 4/1998 |
| WO | 98/52941 | 11/1998 |
| WO | 99/02497 | 1/1999 |
| WO | 99/27965 | 6/1999 |
| WO | 99/46232 | 9/1999 |
| WO | 01/00610 | 1/2001 |

OTHER PUBLICATIONS

Huggins et al., Proceedings of the National Academy of Sciences of the United States of America, vol. 53, No. 4 (Apr. 15, 1965), pp. 791-796.*
Morgan et al., Journal of the Chemical Society, 1965, pp. 3887-3890.*
Vippagunta (Adv. Drug Del. Rev., 2001, vol. 48, 2001, pp. 3-26).*
JP 2001131151A (2001), enclosed English-translated abstract).*
Ludmila Leite et al., "Vasodilating and antiarrhythmic activity of heteryl lactones", Eur. J. Med. Chem., 34, pp. 859-865, 1999.
Svein Dueland et al., "Cholesterol 7α-hydroxylase influences the expression of hepatic apoA-I in two inbred mouse strains displaying different susceptibilities to atherosclerosis and in hepatoma cells", Journal of Lipid Research, vol. 38, pp. 1445-1453, 1997.
Edward M. Rubin et al., "Inhibition of early atherogenesis in transgenic mice by human apolipoprotein AI", Letters to Nature, vol. 353, pp. 265-267, 1991.
Andrew S. Plump et al., "Human apolipoprotein A-I gene expression increases high density lipoprotein and suppresses atherosclerosis in the apolipoprotein E-deficient mouse", Proc. Natl. Acad. Sci., USA, vol. 91, pp. 9607-9611, 1994.
Akira Miyazaki et al., "Intravenous Injection of Rabbit Apolipoprotein A-I Inhibits the Progression of Atherosclerosis in Cholesterol-Fed Rabbits", Arterioscler. Thromb. Vasc. Biol., 15, pp. 1882-1888, 1995.
Siegfried Hünig et al., "Synthesis of 1,4-dipyridyl and 1,4-diquinolyl-butadienes by the Wittig reaction in a two-phase system", Tetrahedron Letters, No. 36, pp. 3151-3154, 1974.
V. Skala et al., "Stilbazoles Derived from 2,6-Dimethyl-3,5-Dicyanopyridine and Their 1,4-Dihydro Derivatives", Collection Czechoslov. Chem. Commun., vol. 40, pp. 1892-1900, 1975.
Hughes et al., "Some Hypocholesteremic 2,3-Diphenylacrylonitriles", Journal of Medicinal Chemistry, 1964, 7(4), pp. 511-518.
International Search Report issued in PCT/JP01/07981 mailed Oct. 30, 2001.

* cited by examiner

*Primary Examiner* — Kevin E Weddington
(74) *Attorney, Agent, or Firm* — Wenderoth, Lind & Ponack, L.L.P.

(57) ABSTRACT

Compounds having an activity to enhance the expression of apoAI are provided. Compounds of formula (I):

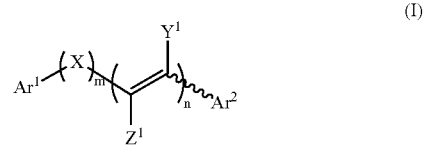

(I)

in which $Ar^1$ and $Ar^2$ are independently a phenyl, naphthyl, or monocyclic or bicyclic aromatic heterocyclic group, which may be optionally substituted; —X— is —N=$CZ^2$—, —$CY^2$=$CZ^2$—, —$CY^2Y^3$—$CHZ^2$—, —S—, —O—, or the like; $Y^1$, $Y^2$, $Y^3$, $Z^1$ and $Z^2$ are independently a hydrogen, a halogen, a lower alkyl, a phenyl, or the like; $Z^1$ and $Z^2$ may be independently a linker group that may combine with $Ar^2$ and $Ar^1$ to form a condensed ring; m is 0 or 1, and n is 0 to 2; a prodrug thereof, a pharmaceutically acceptable salt or solvate thereof; are disclosed.

9 Claims, No Drawings

UTILITIES OF OLEFIN DERIVATIVES

This application is a Divisional Application of U.S. Ser. No. 10/489,365, filed Apr. 19, 2004, which is a 371 Application of PCT/JP01/07981, filed Sep. 14, 2001.

FIELD OF THE INVENTION

This invention relates to a method for enhancing the expression of apolipoprotein AI, and novel compounds therefor.

BACKGROUND ART

Cholesterol is well known as a main etiologic factor for arteriosclerosis that causes severe heart diseases. Especially, increased levels of serum low density lipoprotein (LDL) are believed to be a definite risk factor for coronary heart diseases (CHDs). Remedies for decreasing the level of LDL-cholesterol (LDL-C) in plasma by use of statins have been shown to be clinically effective in preventing the onset of CHDs and improving the conditions of CHDs and survivals in patients suffering from hypercholesterolemia. However, about 40% of CHDs patients have a normal level of LDL-C, and are not always cured effectively by remedies for decreasing the level of LDL-C. On the other hand, it has been known that a half of CHDs patients having a normal level of LDL-C shows a lower level of high density lipoprotein (HDL) cholesterol (HDL-C).

Recently, the lower level of serum HDL-C has been shown to be an additional risk factor of the onset and the recurrence of CHD.

HDL plays an important role in reverse cholesterol transport system that is known as a biological mechanism to transfer an excess cholesterol in cells back to liver so as to maintain the level of cholesterol in living bodies normally.

Lipoproteins such as HDL is mainly comprised of lipids and proteins called apoprotein, and HDL comprises an apoprotein as referred to apolipoprotein AI (hereinafter, made up by apoAI) as a main component.

Excess free cholesterols (FCs) and phospholipids in peripheral cells are extracted by free apoAI to form lipoproteins called preβ-HDL(s). The excess FCs integrated in the preβ-HDLs are transformed into cholesteryl esters (CEs) by lecithin: cholesterol acyl transferase (LCAT), while the preβ-HDLs increase in their particle size to mature into spherical HDLs (HDL3s). The matured HDLs are classified into diverse subfractions based on the density, and these particles further grow up to form HDL2(s). CEs are continuously transferred into very low density lipoprotein (VLDL) and LDL by means of cholesteryl ester-transporter protein (CETP). Those lipoproteins that integrate CEs are finally taken into the liver via receptors. During the course, apoAI is regenerated, and again interacts with peripheral cells to repeat the extraction of cholesterols and the regeneration of preβ-HDLs.

It has been well understood that HDL plays a central role in reverse cholesterol transport system and is a defensive factor of arteriosclerosis. It is expected that agents that promote the HDL functions could be clinically effective as medicaments for treating arteriosclerotic diseases. Accordingly, studies to develop agents that enhance the level of HDL in plasma have been conducted via various approaches.

Among them, one of the most promising approaches is to enhance the serum level of apoAI, a main component of HDL. It is acknowledged that apoAI production increased by enhancing the expression of apoAI gene leads to directly the elevation of HDL-C level in plasma, resulting in the activation of reverse cholesterol transport system. In fact, it has been demonstrated that the mRNA level of apoAI in liver correlates closely with the levels of apoAI and HDL-C in blood (Dueland S., France D., Wang S L., Trawick J D., and Davis R A., J. Lipid Res., 38:1445-53 (1997), "Cholesterol 7 alpha-hydroxylase influences the expression of hepatic apoA-I in two inbred mouse strains displaying different susceptibilities to atherosclerosis and in hepatoma cells."). In addition, it has been shown that apoAI-transgenic mice and rabbit pathologic models administered with apoAI exhibit anti-arteriosclerosis activities (Rubin E. M., Krauss R. M., Spangler E. A., Verstuyft J. G., and Clift S. M., Nature 353, 265-267 (1991), "Inhibition of early atherogenesis in transgenic mice by human apolipoprotein AI."; Plump A. S., Scott C. J., Breslow J. L., Proc. Natl. Acad. Sci. USA., 91, 9607-9611 (1994), "Human apolipoprotein A-I gene expression increases high density lipoprotein and suppress atherosclerosis in the apolipoprotein E-deficient mouse."; Miyazaki A., Sakuma S., Morikawa W., Takiue T., Miake F., Terano T., Sakai M., Hakamata H., Sakamoto Y., et al., Arterioscler. Thromb. Vasc. Biol., 15, 1882-1888 (1995), "Intravenous injection of rabbit apolipoprotein A-I inhibits the progression of atherosclerosis in cholesterol-fed rabbits.").

All these facts clearly suggest that agents that enhance the expression of apoAI would be candidates for medicaments of dyslipidemia, arteriosclerotic diseases, and other diverse diseases associated with HDL.

Compounds that increase apoAI are described in Japanese Patent Publication (kokai) No. 221959/1993, Japanese Patent Publication (kokai) No. 291094/1996, and WO97/09048, but those compounds are different from the compounds according to the present invention in terms of chemical structure.

Structurally similar compounds to those described in the invention have been disclosed in WO97/32574, Japanese Patent Publication (kokai) No. 175965/1989, Japanese Patent Publication (kokai) No. 34967/1991, Tet. Lett., 1974, 36, 3151, Japanese Patent Publication (kokai) No. 50930/1992, Collect. Czech. Chem. Commun., 1975, 40, 1892, WO96/39387, WO98/52941, WO99/02497, and U.S. Pat. No. 5,919,970, however an activity to enhance the expression of apoAI has not been described.

DISCLOSURE OF THE INVENTION

The present invention is directed to methods for enhancing the expression of apoAI, and novel compounds having the activity thereof.

Specifically, the invention provides
1) A method of enhancing the expression of apoAI, which comprises administrating a therapeutically effective amount of a compound of formula (I):

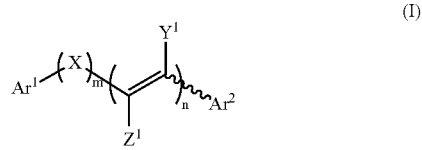

in which
$Ar^1$ and $Ar^2$ are independently a phenyl that may be optionally substituted, a naphthyl that may be optionally substituted, or a monocyclic or bicyclic aromatic heterocyclic group that may be optionally substituted;

—X— is a group of formula (α):

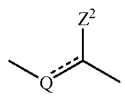

wherein
the broken line is the presence or absence of a bond;
-Q= is a group of

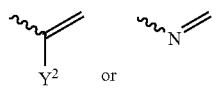

when the broken line is the present of a bond;
the wavy line represents a cis- or trans-geometrical isomerism with respect to the double bond; and
-Q- is —$CY^2Y^3$— or —$NY^4$— when the broken line is the absence of a bond;
or —X— is -β- wherein -β- is —$CY^2Y^3$—, —$NY^4$—, —S— or —O—;
$Y^1$, $Y^2$, $Y^3$, $Z^1$ and $Z^2$ are independently a hydrogen, a halogen, a lower alkyl that may be optionally substituted, a carboxy, a lower alkoxycarbonyl that may be optionally substituted, a cyano, a monocyclic carbocyclic group that may be optionally substituted, or a monocyclic heterocyclic group that may be optionally substituted, and two $Y^1$s or more and two $Z^1$s or more each may be different one another;
$Y^4$ is a hydrogen or a lower alkyl;
$Z^1$ and $Z^2$ may be independently a linker group comprising 1 to 2 atoms that may combine with the constituent atoms of the rings $Ar^2$ and $Ar^1$ that are bonded to $Z^1$ and $Z^2$, via the two atoms respectively, to form a condensed ring;
m is 0 or 1;
n is 0, 1, or 2; provided that, when n is 0, then m is 1 and —X— is a group of formula (α);
the wavy line represents a cis- or trans-geometrical isomerism with respect to the double bond;
provided that, when both $Ar^1$ and $Ar^2$ are a phenyl that may be optionally substituted, then none of $Y^1$, $Y^2$, $Z^1$ and $Z^2$ are a phenyl that may be optionally substituted; a prodrug thereof, a pharmaceutically acceptable salt or solvate of them to a patient expected to enhance the expression of apoAI;
2) The method according to above 1), in which at least one of $Ar^1$ and $Ar^2$ in formula (I) is a monocyclic or bicyclic aromatic heterocyclic group that may be optionally substituted, and that contains a nitrogen atom at the position adjacent to the constituent atom of the ring that has a binding bond;
3) The method according to above 1), in which at least one of $Ar^1$ and $Ar^2$ in formula (I) is 2-pyridyl, 2-quinolyl, 2-quinoxaloyl, 2-benzisoxazolyl, 2-benzothiazolyl, or 2-benzimidazolyl, each of which may be optionally substituted;
4) The method according to above 2) or 3), in which one of $Ar^1$ and $Ar^2$ in formula (I) is a group as defined in above 2) or 3), and the other is a phenyl that may be optionally substituted, or a monocyclic or bicyclic aromatic heterocyclic group that may be optionally substituted;
5) The method according to above 2) or 3), in which one of $Ar^1$ and $Ar^2$ in formula (I) is a group as defined in above 2) or 3), and the other is a phenyl or a monocyclic or bicyclic aromatic heterocyclic group, each of which may be optionally substituted, wherein the substituent is a halogen; a lower alkyl optionally substituted by a halogen or a lower alkoxy; a hydroxy; a lower alkoxy; a phenyloxy; a naphthyloxy; an acyloxy; a carboxy; a lower alkoxycarbonyl; an amino optionally substituted by a lower alkyl or a lower acyl; a phenyl that may be optionally substituted by a lower alkoxy; a nitro; a lower alkylthio; a cyano; a monocyclic heterocyclic group; or an alkylenedioxy that may be substituted by a lower alkyl, a lower alkoxy or phenyl;
6) The method according to any one of above 1) to 5), in which $Y^1$, $Y^2$, $Y^3$, and $Y^4$ in formula (I) is a hydrogen;
7) The method according to any one of above 1) to 6), in which $Z^1$, and $Z^2$ in formula (I) is a hydrogen;
8) The method according to any one of above 1) to 6), in which $Z^1$ in formula (I) is a linker group comprising 1 to 2 atoms that combines with the constituent atoms of the ring $Ar^2$ that are bonded to $Z^1$ via the two atoms to form a condensed ring;
9) The method according to any one of above 1) to 7), in which m in formula (I) is 1, —X— is a group of formula (α), the broken line is the presence of a bond, -Q= is a group of

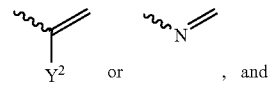

$Y^2$ is a hydrogen;
10) The method according to any one of above 1) to 6), in which m in formula (I) is 1, —X— is a group of formula (α), and $Z^2$ is a linker group comprising 1 to 2 atoms that combines with the constituent atoms of the ring $Ar^1$ to form a condensed ring;
11) The method according to any one of above 1) to 7), in which m and n in formula (I) are 1, and —X— is -β-;
12) A method of prevention or treatment of dyslipidemia or arteriosclerotic diseases, which comprises administrating a therapeutically effective amount of a compound of formula (I) as defined in above 1), a prodrug thereof, a pharmaceutically acceptable salt or solvate of them to a patient suspected to have dyslipidemia or arteriosclerotic diseases; preferably the method thereof which comprises administrating a therapeutically effective amount of the compound as defined in any one of above 2) to 11), a prodrug thereof, a pharmaceutically acceptable salt or solvate of them;
13) A compound of formula (II):

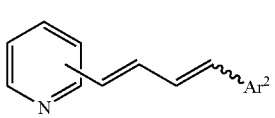

in which
$Ar^2$ is 3-pyridyl, furyl, thienyl, pyrrolyl, or thiazolyl, each of which may be optionally substituted; a prodrug thereof, a pharmaceutically acceptable salt or solvate of them;
14) The compound according to above 13), in which the group:

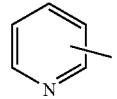

is 2-pyridyl; a prodrug thereof, a pharmaceutically acceptable salt or solvate of them;

15) The compound according to above 13) or 14), in which Ar$^2$ is 3-pyridyl, 3-furyl, 3-thienyl, or 1,3-thiazol-2-yl; a prodrug thereof, a pharmaceutically acceptable salt or solvate of them;

16) A pharmaceutical composition, which comprises the compound according to any one of above 13) to 15), a prodrug thereof, a pharmaceutically acceptable salt or solvate of them, together with a pharmaceutically acceptable additive;

17) The pharmaceutical composition according to above 16), which is used to enhance the expression of apoAI; and 18) The pharmaceutical composition according to above 16), which is used for prevention and/or treatment of dyslipidemia or arteriosclerotic diseases.

Further, the invention provides a method of enhancing the expression of apoAI, and a method of prevention or treatment of dyslipidemia or arteriosclerotic diseases, both of which comprises administrating a therapeutically effective amount of a compound of formula (II) as described above: a prodrug thereof, a pharmaceutically acceptable salt or solvate of them.

The term "halogen" as used herein includes fluorine, chlorine, bromine and iodine.

The term "lower alkyl" as used herein refers to a straight or branched chain alkyl comprising 1 to 6 carbon atoms, preferably 1 to 3 carbon atoms. Examples of the lower alkyl include methyl, ethyl, n-propyl, isopropyl, n-butyl, isobutyl, sec-butyl, tert-butyl, n-pentyl, isopentyl, neopentyl, hexyl, isohexyl, and the like.

The term "lower alkyl that may be optionally substituted" as used herein includes a lower alkyl, of which any position may be substituted by one or more substituents. The substituent includes a halogen, a hydroxy, a lower alkoxy, a monocyclic or bicyclic carbocyclic group, an acyl, an acyloxy, a carboxy, a lower alkoxycarbonyl, an amino, a lower alkylamino, a nitro, a monocyclic or bicyclic heterocyclic group, and the like.

Alkyl moiety of "lower alkoxy", "lower alkylthio" or "lower alkylamino" is similar to the "lower alkyl" as described above.

The term "alkylenedioxy" specifically includes methylenedioxy, ethylenedioxy, and the like.

Lower alkyl moiety of "lower alkoxycarbonyl" is similar to the "lower alkyl" as described above, and substituent of "lower alkoxycarbonyl that may be optionally substituted" is similar to the substituent of "lower alkyl that may be optionally substituted" as described above.

The term "acyl" includes an aroyl and an aliphatic acyl containing 1 to 7 carbon atoms. Here, "aroyl" refers to an aromatic acyl group formed by deleting a hydroxy from an aromatic carbocyclic acid. Examples of the acyl include formyl, acetyl, propionyl, butyryl, isobutyryl, valeryl, pivaloyl, hexanoyl, acryloyl, propioloyl, methacryloyl, crotonoyl, and benzoyl.

Acyl moiety of "acyloxy" is similar to the "acyl".

The term "monocyclic carbocyclic group" as used herein refers to a cyclic ring group containing 3 to 10 carbon atoms, preferably 5 to 8 carbon atoms, and includes an aromatic and non-aromatic cyclic ring group. Examples of the carbocyclic group include cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl, cyclononyl, cyclodecyl, and phenyl.

The term "monocyclic heterocyclic group" refers to a cyclic ring group wherein one or more carbon atoms that are contained in the "monocyclic carbocyclic group" as described above and that can be substituted, is (are) substituted by a hetero atom selected from the group consisting of N, S and O. Examples include aromatic heterocyclic groups such as pyrrolyl, imidazolyl, pyrazolyl, pyridyl, pyridazinyl, pyrimidyl, pyrazinyl, triazolyl, triazinyl, tetrazolyl, isoxazolyl, oxazolyl, oxadiazolyl, isothiazolyl, thiazolyl, thiadiazolyl, furyl, and thienyl; and non-aromatic heterocyclic groups such as dioxanyl, dioxozinyl, dioxolanyl, dioxolyl, dithiazinyl, imidazolidinyl, imidazolinyl, morpholyl, oxazinyl, oxadiazoyl, furazanyl, oxathiazyl, oxathiazinyl, oxathiolanyl, oxazolidinyl, oxazolinyl, piperazinyl, piperidinyl, pyranyl, pyrazolidinyl, pyrazolinyl, pyrrolidinyl, pyrrolinyl, tetrahydropyranyl, thiadiazolidinyl, thienyl, thiazinyl, thiadiazinyl, thioranyl, and thiolanyl. Preferred ones include pyridyl, pyrimidinyl, pyrrolyl, furyl, thienyl, and thiazolyl.

Heterocyclic moiety of "monocyclic aromatic heterocyclic oxy" is similar to the aromatic heterocyclic group as described above.

The term "bicyclic carbocyclic group" refers to an aromatic or non-aromatic cyclic group containing 6 to 12 carbon atoms wherein two cyclic rings are condensed. Examples include naphthyl, indanyl, indenyl, dihydronaphthyl, and tetrahydronaphthyl, and preferably, naphthyl.

The term "bicyclic heterocyclic group" includes a cyclic ring compound wherein one or more carbon atoms that are contained in the "bicyclic carbocyclic group" as described above and that can be substituted, is (are) substituted by a hetero atom selected from the group consisting of N, S and O. Examples include indolyl, isoindolyl, indolizinyl, benzimidazolyl, indazolyl, cinnolinyl, phthalazinyl, benzoxazolyl, benzisoxazolyl, benzoxadiazolyl, benzothiazolyl, benzisothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, quinolyl, isoquinolyl, quinoxalinyl, purinyl, pteridinyl, naphthylidinyl, and pyrazinopyridazinyl. Preferable examples include indolyl, benzimidazolyl, benzoxazolyl, benzoxadiazolyl, benzothiazolyl, benzothiadiazolyl, benzofuryl, benzothienyl, imidazopyridyl, triazolopyridyl, quinolyl, isoquinolyl, and quinoxalinyl.

The term "aromatic heterocyclic group" refers to only an aromatic heterocyclic group among the groups of "heterocyclic group" as described above.

Substituent in "monocyclic or bicyclic carbocyclic group that may be optionally substituted", "phenyl that may be optionally substituted", "naphthyl that may be optionally substituted", and "monocyclic carbocyclic group that may be optionally substituted" includes a halogen; a hydroxy; a lower alkyl optionally substituted by a halogen, a hydroxy, or a lower alkoxy; a lower alkoxy optionally substituted by a halogen, a hydroxy, a carboxy, or a lower alkoxycarbonyl; a lower alkenyl optionally substituted by a halogen or a hydroxy; a lower alkenyloxy optionally substituted by a halogen or a hydroxy; a lower alkylthio; a non-aromatic carbocyclic group optionally substituted by a halogen, a hydroxy, or a lower alkyl; an acyl; an acyloxy; a carboxy; a lower alkoxycarbonyl; a lower alkenyloxycarbonyl; an amino optionally substituted by a lower alkyl or an acyl; a hydrazino, a nitro; a cyano; a phenyl or naphthyl optionally substituted by a halogen, a hydroxy, a lower alkyl or a lower alkoxy; a heterocyclic group; a phenoxy optionally substituted by a halogen, a hydroxy, or a lower alkyl; a monocyclic aromatic heterocyclic oxy; an oxo; and an alkylenedioxy optionally substituted by a lower alkyl, a lower alkoxy, a phenyl or the like; all of which may be bonded at one or more arbitrary positions.

Preferable examples include a halogen; a hydroxy; a lower alkyl optionally substituted by a halogen or a hydroxy; a lower alkoxy optionally substituted by a halogen, a hydroxy, a carboxy, or a lower alkoxycarbonyl; a lower alkenyl; a lower alkylthio; an acyl; an acyloxy; a carboxy; a lower alkoxycarbonyl; an amino optionally substituted by a lower alkyl or an acyl; a hydrazino, a nitro; a cyano; a phenyl; a heterocyclic group; a phenoxy; and an alkylenedioxy.

Substituent in "monocyclic aromatic heterocyclic group that may be optionally substituted", "monocyclic heterocyclic group that may be optionally substituted", "monocyclic aromatic heterocyclic group that may be optionally substituted", "monocyclic or bicyclic aromatic heterocyclic group that may be optionally substituted", "2-pyridyl that may be optionally substituted", "2-pyridyl, 2-quinolyl, 2-quinoxaloyl, 2-benzisoxazolyl, 2-benzothiazolyl, or 2-benzimidazolyl, each of which may be optionally substituted", and "3-pyridyl, furyl, thienyl, pyrrolyl, or thiazolyl, each of which may be optionally substituted" is similar to the substituent in "monocyclic or bicyclic carbocyclic group that may be optionally substituted" and the like as described above. Preferable examples include a halogen; a hydroxy; a lower alkyl optionally substituted by a lower alkoxy; a lower alkoxy; a lower alkenyl; a lower alkylthio; an acyl; an acyloxy; a carboxy; a lower alkoxycarbonyl; an amino optionally substituted by a lower alkyl; and a phenyl optionally substituted by a lower alkoxy; and a monocyclic heterocyclic group.

The term "a monocyclic or bicyclic aromatic heterocyclic group that contains a nitrogen atom at the position adjacent to the constituent atom of the ring that has a binding bond" includes "a monocyclic or bicyclic aromatic heterocyclic group" as described above that has, at ortho position with respect to the constituent N atom of a ring, a binding bond to:

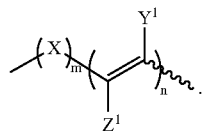

Specific examples include monocyclic aromatic heterocyclic groups such as 2-pyridyl, 2- or 4-pyrimidinyl, 3-pyridazinyl, 2-pyrazinyl, 1,3,5-triazin-2-yl, 2-pyrrolyl, 1- or 3-pyrazolyl, 2- or 4-imidazolyl, 2- or 4-oxazolyl, 3-isoxazolyl, 1,3,4-oxadiazol-2-yl, 1,3-thiazol-2-yl, 1,3-thiazol-4-yl, 1,2,5-thiadiazol-3-yl, 1,2,3-thiadiazol-4-yl, 1,3,4-thiadiazol-2-yl, 3-isothiazolyl, 1,2,3-triazol-4-yl, 1H-tetrazol-1-yl, and 1H-tetrazol-5-yl; and bicyclic aromatic heterocyclic groups such as 2-benzimidazolyl, 3-benzisothiazolyl, 3-benzisoxazolyl, 2-benzoxazolyl, 2-benzothiazolyl, 1-benzotriazolyl, 1- or 3-indazolyl, 3-cinnolinyl, 2-indolyl, 1- or 3-isoindolyl, 2-[1.7]-naphthylidinyl, 2-, 4-, 6- or 7-pteridinyl, 2-, 6 or 8-purinyl, 1- or 3-isoquinolyl, 2-quinolyl, 2- or 4-quinazolinyl, and 2-quinoxalinyl.

The phrase "a monocyclic or bicyclic aromatic heterocyclic group that may be optionally substituted, and that contains a nitrogen atom at the position adjacent to the constituent atom of the ring that has a binding bond" means that one or more substituents may be bonded at arbitrary positions, similarly to "monocyclic or bicyclic carbocyclic group that may be optionally substituted" as described above.

The term "linker group comprising 1 to 2 atoms" refers to a group wherein the number of the atom (except for hydrogen atom) comprised in a linker group is 1 or 2, includes a linker formed by 1 or 2 groups that are arbitrarily selected from a group consisting of —$CR^1R^2$—, —O—, —$NR^3$—, and —S—. The bond between the two groups may be a double bond, if possible. Examples include linker groups comprising 1 to 2 atoms such as —$CR^1R^2$—, —O—, —$NR^3$—, —S—, —$(CR^1R^2)_2$—, —$CR^1R^2O$—, —$CR^1R^2NR^3$—, —$CR^1R^2S$—, —$OCR^1R^2$—, —$NR^3CR^1R^2$—, —S$CR^1R^2$—, —$CR^1=CR^1$—, —$CR^1=N$—, —N=$CR^1$—, and —N=N— wherein $R^1$, $R^2$ and $R^3$ are independently a hydrogen, a halogen, a hydroxy, a lower alkyl, a lower alkoxy, or an amino, or $R^1$ and $R^2$ may be combined together to form an oxo, and two $R^1$s or more and two $R^2$s or more each may be different one another. Preferable examples include a linker wherein $R^1$, $R^2$ and $R^3$ are a hydrogen, and more preferable ones include —S—, —O—, —$NR^3$—, —$CR^1=CR^1$—, —$CR^1=N$—, and —N=$CR^1$—.

The phrase "$Ar^2$ that are bonded to $Z^1$ via the two atoms" means that $Ar^2$ and $Z^1$ have a relationship as shown below:

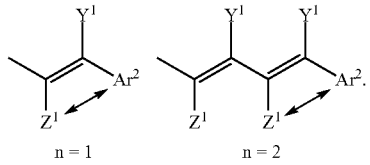

Alternatively, the phrase "$Ar^1$ that are bonded to $Z^2$ via the two atoms" in case that m is 1, and X is a group of formula (α) means that $Ar^1$ and $Z^2$ have a relationship as shown below:

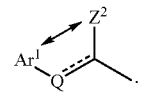

The phrase "$Z^1$ and $Z^2$ may be independently a linker group comprising 1 to 2 atoms that may combine with the constituent atoms of the rings $Ar^2$ and $Ar^1$—to form a condensed ring" means that $Z^1$ or $Z^2$, that is used as a constituent atom of a ring, is combined with $Ar^2$ and/or $Ar^1$ to form a condensed ring. Specifically, the phrase means the following group is formed:

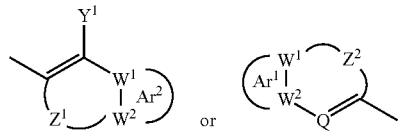

wherein the atoms as indicated by $W^1$ and $W^2$ may be either a carbon atom or a nitrogen atom. Examples of the condensed cyclic ring group formed according to the definition include 2-naphthyl, 2-, 5- or 6-benzofuryl, 2-, 5- or 6-benzimidazolyl, 2-, 5- or 6-benzothiazolyl, 5-benzisothiazolyl, 5- or 6-benzisoxazolyl, 2-, 5- or 6-benzoxazolyl, 5-benzotriazolyl, 5- or 6-benzoxadiazolyl, 2-, 5- or 6-benzothienyl, 3-, 5- or 6-cinnolinyl, 5- or 6-indazolyl, 2-, 5- or 6-indolyl, 5-isoindolyl, 3-, 6- or 7-isoquinolyl, 2- or 6-quinazolinyl, 2-, 3-, 6- or 7-quinolyl, 2- or 6-quinoxalinyl, 3-, 6- or 7-1H-isochromenyl, 3-, 6- or 7-2H-chromenyl, 3-thiochromenyl, 3-, 6- or 7-1,2-dihydroquinolinyl, 2- or 3-[1, 7]naphthylidinyl, and 6-phthalazinyl.

The compounds according to the invention include pharmaceutically acceptable, producible salts. Examples of the "pharmaceutically acceptable salts" include a salt with an inorganic acid e.g. those with hydrochloric acid, sulfuric acid, nitric acid, phosphoric acid, or the like; a salt with an organic acid e.g. those with p-toluenesulfonic acid, methanesulfonic acid, oxalic acid, citric acid, or the like; a salt with an organic base e.g. ammonium, trimethylammonium, triethylammonium, or the like; a salt with an alkaline metal e.g. sodium or potassium, or the like; a quaternary salt with alkyl halide e.g., methyl iodide, ethyl iodide or the like; and a salt with an alkaline earth metal e.g., calcium or magnesium, or the like.

The compounds according to the invention may form solvates as coordinated with a suitable organic solvent and/or water. Hydrates are exemplified.

The compounds according to the invention also include prodrugs. In the context of the invention, a "prodrug" is a derivative of a compound according to the invention comprising a chemically or metabolically cleavable group. In the course of metabolism in the body, a prodrug shows a pharmacological activity as a result of conversion to the compounds according to the invention. Method for selecting and producing suitable prodrug derivatives are described in, e.g. "Design of Prodrugs, Elsevier, Amsterdam (1985)".

Prodrugs of compound (I) according to the invention having a carboxy are exemplified by an ester derivative prepared by condensing the carboxy group of compound (I) with a suitable alcohol, and alternatively by an amide derivative prepared by reacting the carboxy group of compound (I) and a suitable amine.

Prodrugs of compound (I) according to the invention having a hydroxy are exemplified by an acyloxy derivative prepared by reacting the hydroxy group of compound (I) and a suitable acyl halide or a suitable acid anhydride.

Prodrugs of compound (I) according to the invention having an amino are exemplified by an amide derivative prepared by reacting the amino group of compound (I) and a suitable acid halide or a suitable mixed anhydride compound.

When compound (I) according to the invention has asymmetric carbon atom(s), then the invention encompasses a racemic mixture, both of enantiomers, and all of diastereomers. When compound (I) according to the invention has a double bond, the invention include both of geometric isomers resulting from possible arrangements of its substituents.

Although all of the compounds according to the invention have an activity for enhancing the expression of apoAI, the following compounds can be listed as preferable compounds. In formula (I):

a compound wherein $Ar^1$ is a phenyl or naphthyl that may be optionally substituted wherein the substituent is a halogen; a lower allyl optionally substituted by a halogen; a hydroxy; a lower alkoxy; an aryloxy; an acyloxy; a carboxy; a lower alkoxycarbonyl; an amino optionally substituted by a lower alkyl or a lower acyl; a phenyl; a nitro; a lower alkylthio; a cyano; a monocyclic heterocyclic group; or an alkylenedioxy (hereinafter, regarded as Ar1-a);

a compound wherein $Ar^1$ is an unsubstituted phenyl or an unsubstituted naphthyl (hereinafter, regarded as $Ar^1$-b);

a compound wherein $Ar^1$ is a monocyclic or bicyclic aromatic heterocyclic group that may be optionally substituted (hereinafter, regarded as Ar1-c);

a compound wherein $Ar^1$ is a monocyclic or bicyclic aromatic heterocyclic group that may be optionally substituted wherein the substituent is a lower alkyl or an amino (hereinafter, regarded as Ar1-d);

a compound wherein $Ar^1$ is a monocyclic or bicyclic heterocyclic group that contains a nitrogen at the ortho position, and that may be optionally substituted (hereinafter, regarded as Ar1-e);

a compound wherein $Ar^1$ is a monocyclic or bicyclic heterocyclic group that contains a nitrogen at the ortho position, and that may be optionally substituted wherein the substituent is a lower alkyl or an amino (hereinafter, regarded as Ar1-f);

a compound wherein $Ar^1$ is 2-quinolyl, 2-quinoxaloyl, 2-benzimidazolyl, 2-thiazolyl, 2-benzothiazolyl, 2-oxazolyl, 2-benzoxazolyl, 2-oxadiazolyl, 2-pyridyl, 2-pyrimidyl, or 2-imidazolyl (hereinafter, regarded as Ar1-g);

a compound wherein m is 0, and n is 1 (hereinafter, regarded as X-a);

a compound wherein m is 0, and n is 2 (hereinafter, regarded as X-b);

a compound wherein m is 1, n is 0, X is a group of formula (α), and Q is —N═ (hereinafter, regarded as X-c);

a compound wherein m and n are 1, X is a group of formula (α), and Q is —CH₂— or —N═ (hereinafter, regarded as X-d);

a compound wherein m is 1, n is 2, X is a group of formula (α), and Q is —CH═ (hereinafter, regarded as X-e);

a compound wherein m and n are 1, X is $CH_2CH_2$ or S (hereinafter, regarded as X-f);

a compound wherein $Y^1$ and $Z^1$ are a hydrogen (hereinafter, regarded as YZ-a);

a compound wherein $Y^1$ and $Z^1$ are independently a hydrogen, a halogen, a lower alkyl, or a cyano (hereinafter, regarded as YZ-b);

a compound wherein $Y^1$ is a hydrogen, and $Z^1$ is a linker group comprising 1 to 2 atoms (hereinafter, regarded as YZ-c);

a compound wherein $Ar^2$ is a phenyl or naphthyl that may be optionally substituted wherein the substituent is a halogen; a lower allyl optionally substituted by a halogen; a hydroxy; a lower alkoxy; an aryloxy; an acyloxy; a carboxy; a lower alkoxycarbonyl; an amino optionally substituted by a lower alkyl or a lower acyl; a phenyl; a nitro; a lower alkylthio; a cyano; a monocyclic heterocyclic group; or a lower alkylenedioxy (hereinafter, regarded as Ar2-a);

a compound wherein $Ar^2$ is a monocyclic or bicyclic aromatic heterocyclic group that may be optionally substituted (hereinafter, regarded as Ar2-b);

a compound wherein $Ar^2$ is a monocyclic or bicyclic aromatic heterocyclic group that may be optionally substituted wherein the substituent is a lower alkyl, a lower alkoxy, a lower alkoxy(a lower allyl), a halogen, a lower alkoxycarbonyl, a phenyl, a lower alkoxyphenyl, or a monocyclic heterocyclic group (hereinafter, regarded as Ar2-c);

a compound wherein $Ar^2$ is furyl, thiazolyl, or a pyrrolyl, thienyl, imidazolyl or pyridyl, each of which may be optionally substituted (hereinafter, regarded as Ar2-d);

a compound wherein a combination of $Ar^1$; m, n, and X; and $Y^1$ and $Z^1$; $Ar^2$ (Ar1, X, YZ, Ar2) is any one of the followings: (Ar1, X, YZ, Ar2)=(Ar1-a, X-a, YZ-a, Ar2-b), (Ar1-a, X-a, YZ-a, Ar2-d), (Ar1-b, X-a, YZ-a, Ar2-b), (Ar1-b, X-a, YZ-a, Ar2-d), (Ar1-c, X-a, YZ-a, Ar2-a), (Ar1-c, X-a, YZ-a, Ar2-b), (Ar1-c, X-a, YZ-a, Ar2-c), (Ar1-c, X-a, YZ-a, Ar2-d), (Ar1-e, X-a, YZ-a, Ar2-a), (Ar1-e, X-a, YZ-a, Ar2-b), (Ar1-e, X-a, YZ-a, Ar2-c), (Ar1-e, X-a, YZ-a, Ar2-d), (Ar1-g, X-a, YZ-a, Ar2-a), (Ar1-g, X-a, YZ-a, Ar2-b), (Ar1-g, X-a, YZ-a, Ar2-c), (Ar1-g, X-a, YZ-a, Ar2-d), (Ar1-c, X-a, YZ-b, Ar2-b), (Ar1-c, X-a, YZ-b, Ar2-d), (Ar1-e, X-a, YZ-b, Ar2-b), (Ar1-e, X-a, YZ-b, Ar2-d), (Ar1-g, X-a, YZ-b, Ar2-b), (Ar1-g, X-a, YZ-b, Ar2-d), (Ar1-b, X-a, YZ-c, Ar2-a), (Ar1-c, X-a, YZ-c, Ar2-a), (Ar1-a, X-b, YZ-a, Ar2-b), (Ar1-a, X-b, YZ-a, Ar2-d), (Ar1-b, X-b, YZ-a, Ar2-b), (Ar1-b, X-b, YZ-a, Ar2-d), (Ar1-c, X-b, YZ-a, Ar2-a), (Ar1-c, X-b, YZ-a, Ar2-b), (Ar1-c, X-b, YZ-a, Ar2-c), (Ar1-c, X-b, YZ-a, Ar2-d), (Ar1-e, X-b, YZ-a, Ar2-a), (Ar1-e, X-b, YZ-a, Ar2-b), (Ar1-e, X-b, YZ-a, Ar2-c), (Ar1-e, X-b, YZ-a, Ar2-d), (Ar1-g, X-b, YZ-a, Ar2-a), (Ar1-g, X-b, YZ-a, Ar2-b), (Ar1-g, X-b, YZ-a, Ar2-c), (Ar1-g, X-b, YZ-a, Ar2-d), (Ar1-b, X-b, YZ-b, Ar2-b), (Ar1-c, X-b, YZ-b, Ar2-a), (Ar1-c, X-b, YZ-b, Ar2-b), (Ar1-c, X-b, YZ-b, Ar2-d), (Ar1-c, X-b, YZ-c, Ar2-a), (Ar1-c, X-b, YZ-c, Ar2-b), (Ar1-c, X-b, YZ-c, Ar2-d), (Ar1-e, X-b, YZ-c, Ar2-a), (Ar1-e, X-b, YZ-c, Ar2-d), (Ar1-g, X-b, YZ-c, Ar2-a), (Ar1-g, X-b, YZ-c, Ar2-d), (Ar1-b, X-c, YZ-c, Ar2-a), (Ar1-b, X-c, YZ-c, Ar2-b), (Ar1-b, X-c, YZ-c, Ar2-d), (Ar1-b, X-d, YZ-c, Ar2-a), (Ar1-b, X-d, YZ-c, Ar2-b), (Ar1-b, X-d, YZ-c, Ar2-d), (Ar1-c, X-e, YZ-a, Ar2-b), (Ar1-c, X-e, YZ-a, Ar2-d), (Ar1-e, X-e, YZ-a, Ar2-b), (Ar1-e, X-e, YZ-a, Ar2-d), (Ar1-g, X-e, YZ-a, Ar2-b), (Ar1-g, X-e, YZ-a, Ar2-d), (Ar1-c, X-e, YZ-b, Ar2-b), (Ar1-c, X-e, YZ-b, Ar2-d), (Ar1-e, X-e, YZ-b, Ar2-b), (Ar1-e, X-e, YZ-b, Ar2-d), (Ar1-g, X-e, YZ-b, Ar2-b), (Ar1-g, X-e, YZ-b, Ar2-d), (Ar1-b, X-f, YZ-a, Ar2-b), (Ar1-b, X-f, YZ-a, Ar2-d), (Ar1-c, X-f, YZ-a, Ar2-a), (Ar1-e, X-f, YZ-a, Ar2-a), (Ar1-g, X-f, YZ-a, Ar2-a).

(Ar1-c, X-e, YZ-c, Ar2-a), (Ar1-c, X-e, YZ-c, Ar2-b), (Ar1-c, X-e, YZ-c, Ar2-d), (Ar1-e, X-e, YZ-c, Ar2-a), (Ar1-e, X-e, YZ-c, Ar2-b), (Ar1-e, X-e, YZ-c, Ar2-d), (Ar1-g, X-e, YZ-c, Ar2-a), (Ar1-g, X-e, YZ-c, Ar2-b), and (Ar1-g, X-e, YZ-c, Ar2-d); and a prodrug thereof, a pharmaceutically acceptable salt or solvate of them.

Specific compounds are exemplified by the followings:
2-phenylquinoxaline (Ia-1)
2-(4-chlorophenyl)quinoxaline (Ia-2)
2-(4-methoxyphenyl)quinoxaline (Ia-3)
2-(pyridin-3-yl)quinoxaline (Ia-4)
2-(pyridin-3-yl)quinoxaline (Ia-5)
2-(thiophen-3-yl)quinoxaline (Ia-6)
2-(furan-3-yl)quinoxaline (Ia-7)
2-(pyrrol-3-yl)quinoxaline (Ia-8)
2-(thiophen-2-yl)quinoxaline (Ia-9)
2-(biphenyl-4-yl)quinoxaline (Ia-10)
2-(naphthalen-2-yl)quinoxaline (Ia-11)
2-(biphenyl-4-yl)quinoline (Ia-12)
2-phenylquinoline (Ia-13)
2-(4-methoxyphenyl)quinoline (Ia-14)
2-(thiophen-3-yl)quinoline (Ia-15)
2-(4-chlorophenyl)quinoline (Ia-16)
2-biphenyl-4-yl-4-methyl-quinoline (Ia-17)
3-phenylquinoline (Ia-18)
2-(4-methoxyphenyl)-1H-benzimidazole (Ia-19)
2-phenylbenzothiazole (Ia-20)
[2,2']dibenzothiazolyl (Ia-21)
2-(4-methoxyphenyl)benzoxazole (Ia-22)
2-styrylpyridine (Ib-1)
2-(2-p-tolylvinyl)pyridine (Ib-2)
methyl 4-(2-pyridin-2-yl-vinyl)-benzoate (Ib-3)
4-(2-pyridin-2-yl-vinyl)-benzoic acid (Ib-4)
4-(2-pyridin-2-yl-vinyl)benzonitrile (Ib-5)
2-(2-biphenyl-4-yl-vinyl)pyridine (Ib-6)
2-[2-(4-fluorophenyl)vinyl]pyridine (Ib-7)
N-[4-(2-pyridin-2-yl-vinyl)phenyl]acetamide methyl iodide (Ib-8)
2-[2-(4-trifluorophenyl)vinyl]pyridine (Ib-9)
2-[2-(2-hydroxyphenyl)vinyl]pyridine (Ib-11)
2-[2-(4-methoxyphenyl)vinyl]pyridine (Ib-12)
2-(2-benzo[1,3]dioxol-5-yl-vinyl)pyridine (Ib-13)
2-[2-(2,3-dihydrobenzo[1,4]dioxin-6-yl)vinyl]pyridine (Ib-14)
2-(2-naphthalen-2-yl-vinyl)pyridine (Ib-17)
6-(2-pyridin-2-yl-vinyl)quinoline (Ib-19)
6-(2-pyridin-2-yl-vinyl)-1H-indole (Ib-20)
2-(2-benzofuran-5-yl-vinyl)pyridine (Ib-21)
2-(2-benzofuran-6-yl-vinyl)pyridine (Ib-22)
5-(2-pyridin-2-yl-vinyl)-1H-indole (Ib-23)
2-(2-benzothiophene-5-yl-vinyl)pyridine (Ib-24)
5-(2-pyridin-2-yl-vinyl)benzo[1,2,5]thiadiazole (Ib-25)
5-(2-pyridin-2-yl-vinyl)benzo[1,2,5]oxadiazole (Ib-26)
7-(2-pyridin-2-yl-vinyl)imidazo[1,2-a]pyridine (Ib-27)
7-(2-pyridin-2-yl-vinyl)-[1,2,4]triazolo[1,5-a]pyridine (Ib-28)
6-(2-pyridin-2-yl-vinyl)imidazo[1,2-a]pyridine (Ib-29)
3-(2-pyridin-2-yl-vinyl)quinoline (Ib-30)
5-(2-pyridin-2-yl-vinyl)benzothiazole (Ib-31)
6-(2-pyridin-2-yl-vinyl)-[1,2,4]triazolo[1,5-a]pyridine (Ib-32)
2-(2-benzofuran-2-yl-vinyl)pyridine (Ib-33)
2-(2-pyridin-2-yl-vinyl)benzothiazole (Ib-34)
2-(2-benzofuran-3-yl-vinyl)pyridine (Ib-35)
1-methyl-2-(2-pyridin-2-yl-vinyl)-1H-indole (Ib-36)
2-(2-pyridin-2-yl-vinyl)-1H-indole (Ib-37)
2-(2-pyridin-2-yl-vinyl)-1H-benzimidazole (Ib-38)
2-(2-benzo[b]thiophen-2-yl-vinyl)pyridine (Ib-39)
6-(2-pyridin-2-yl-vinyl)quinoxaline (Ib-40)
1,2-bis-(2-pyridyl)ethylene (Ib-41)
1-(2-pyridyl)-2-(3-pyridyl)ethylene (Ib-43)
1-(2-pyridyl)-2-(4-pyridyl)ethylene (Ib-45)
2-[2-(1-methyl-1H-pyrrol-2-yl)vinyl]pyridine (Ib-50)
2-(2-thiophen-3-yl-vinyl)pyridine (Ib-52)
2-styrylquinoxaline (Ib-56)
2-(2-p-tolylvinyl)quinoxaline (Ib-57)
methyl 4-(2-quinoxaline-2-yl-vinyl)-benzoate (Ib-58)
4-(2-quinoxaline-2-yl-vinyl)-benzoic acid (Ib-59)
4-(2-quinoxaline-2-yl-vinyl)benzonitrile (Ib-60)
2-(2-biphenyl-4-yl-vinyl)quinoxaline (Ib-61)
2-(2-naphthalen-2-yl-vinyl)quinoxaline (Ib-62)
2-(2-benzothiophen-6-yl-vinyl)quinoxaline (Ib-63)
2-[2-(4-fluorophenyl)vinyl]quinoxaline (Ib-64)
2-[2-(4-chlorophenyl)vinyl]quinoxaline (Ib-65)
2-[2-(4-bromophenyl)vinyl]quinoxaline (Ib-66)
2-[2-(4-methoxyphenyl)vinyl]quinoxaline (Ib-67)
4-(2-quinoxaline-2-yl-vinyl)phenol (Ib-68)
4-(2-quinoxaline-2-yl-vinyl)phenylamine (Ib-69)
N-[4-(2-quinoxaline-2-yl-vinyl)phenyl]acetamide (Ib-70)
2-[2-(4-dimethylaminophenyl)vinyl]quinoxaline (Ib-71)
2-[2-(4-phenoxyphenyl)vinyl]quinoxaline (Ib-72)
2-(2-furan-2-yl-vinyl)quinoxaline (Ib-73)
2-(2-furan-3-yl-vinyl)quinoxaline (Ib-75)
2-(2-thiazol-5-yl-vinyl)quinoxaline (Ib-76)
2-(2-thiophen-3-yl-vinyl)quinoxaline (Ib-77)
2-[2-(1H-pyrrol-3-yl)vinyl]quinoxaline (Ib-78)
2-[2-(1H-[1,2,3]triazol-4-yl)vinyl]quinoxaline (Ib-79)
[4-(2-benzoxazole-2-yl-vinyl)phenyl]dimethylamine (Ib-80)
2-(2-p-tolyl-vinyl)benzoxazole (Ib-81)
4-(2-benzoxazole-2-yl-vinyl)-benzoic acid (Ib-82)
2-[2-(1-methyl-1H-pyrrol-2-yl)vinyl]benzoxazole (Ib-83)
2-(2-pyridin-2-yl-vinyl)benzoxazole (Ib-84)
[4-(2-benzothiazole-2-yl-vinyl)phenyl]dimethylamine (Ib-85)
4-(2-benzothiazole-2-yl-vinyl)benzonitrile (Ib-86)
2-(2-thiophen-3-yl-vinyl)benzothiazole (Ib-87)
ethyl 4-[3-(2-quinoline-2-yl-vinyl)phenoxy]butanoate (Ib-88)
4-[3-(2-quinoline-2-yl-vinyl)phenoxy]butanoic acid (Ib-89)
2-[2-(4-methoxyphenyl)vinyl]quinoline (Ib-90)
2-(2-thiophen-3-yl-vinyl)benzothiazole (Ib-91)
2-(2-furan-3-yl-vinyl)benzothiazole (Ib-92)
2-(2-1H-pyrrol-3-yl-vinyl)benzothiazole (Ib-93)
2-{2-[4-(1H-pyrrol-2-yloxy)phenyl]vinyl}quinoline (Ib-94)
2-(2-thiophen-3-yl-vinyl)-1H-benzimidazole (Ib-95)
2-(2-biphenyl-4-yl-vinyl)-1H-benzimidazole (Ib-96)
2-[2-(4-methoxyphenyl)vinyl]-1H-benzimidazole (Ib-97)
2-[2-(1H-imidazol-4-yl)vinyl]-1H-benzimidazole (Ib-98)
ethyl 2-[2-(1H-benzimidazole-2-yl)vinyl]oxazol-4-carboxylate (Ib-99)

2-(2-thiophen-2-yl-vinyl)pyridine (Ib-100)
2-pyridin-2-yl-3-thiophen-2-yl-acrylonitrile (Ib-101)
3-[2-(5-phenyl)-[1,3,4]oxadiazol-2-yl-vinyl]pyridine (Ib-102)
3-{2-[(5-(3-methoxyphenyl)-[1,3,4]oxadiazol-2-yl]vinyl}pyridine (Ib-103)
2-(4-phenyl-buta-1,3-dienyl)pyridine (Ic-1)
2-(4-o-tolyl-buta-1,3-dienyl)pyridine (Ic-2)
2-[4-(2,5-dimethylphenyl)buta-1,3-dienyl]pyridine (Ic-3)
2-(4-m-tolyl-buta-1,3-dienyl)pyridine (Ic-4)
2-[4-(3,5-dimethylphenyl)buta-1,3-dienyl]pyridine (Ic-5)
2-(4-p-tolyl-buta-1,3-dienyl)pyridine (Ic-6)
2-[4-(3,4-dimethylphenyl)buta-1,3-dienyl]pyridine (Ic-7)
2-[4-(2,4,6-trimethylphenyl)buta-1,3-dienyl]pyridine (Ic-8)
2-[4-(4-trifluoromethylphenyl)buta-1,3-dienyl]pyridine (Ic-9)
2-[4-(3-trifluoromethylphenyl)buta-1,3-dienyl]pyridine (Ic-10)
2-[4-(4-methoxyphenyl)buta-1,3-dienyl]pyridine (Ic-11)
2-[4-(3-methoxyphenyl)buta-1,3-dienyl]pyridine (Ic-12)
2-[4-(3,4-dimethoxyphenyl)buta-1,3-dienyl]pyridine (Ic-13)
2-[4-(3,4,5-trimethoxyphenyl)buta-1,3-dienyl]pyridine (Ic-14)
2-[4-(4-methoxy-3-methylphenyl)buta-1,3-dienyl]pyridine (Ic-15)
2-[4-(4-methoxy-2,5-dimethylphenyl)buta-1,3-dienyl]pyridine (Ic-16)
2,6-dimethyl-4-(4-pyridin-2-yl-buta-1,3-dienyl)phenol (Ic-17)
phenyl 2-methoxy-4-(4-pyridin-2-yl-buta-1,3-dienyl)acetate (Ic-18)
2-methoxy-4-(4-pyridin-2-yl-buta-1,3-dienyl)phenol (Ic-19)
2-(4-benzo[1,3]dioxol-5-yl-buta-1,3-dienyl)pyridine (Ic-20)
2-[4-(7-methylbenzo[1,3]dioxole)-5-yl-buta-1,3-dienyl]pyridine (Ic-21)
2-[4-(2,3-dihydrobenzo[1,4]dioxin-6-yl)buta-1,3-dienyl]pyridine (Ic-22)
5-(4-pyridin-2-yl-buta-1,3-dienyl)benzo[1,2,5]thiadiazole (Ic-23)
5-(4-pyridin-2-yl-buta-1,3-dienyl)benzo[1,2,5]oxadiazole (Ic-24)
7-(4-pyridin-2-yl-buta-1,3-dienyl)imidazo[1,2-a]pyridine (Ic-25)
7-(4-pyridin-2-yl-buta-1,3-dienyl)-[1,2,4]triazolo[1,5-a]pyridine (Ic-26)
5-(4-pyridin-2-yl-buta-1,3-dienyl)-1,3a,7a-triazaindene (Ic-27)
6-(4-pyridin-2-yl-buta-1,3-dienyl)-[1,2,4]triazolo[1,5-a]pyridine (Ic-28)
6-(4-pyridin-2-yl-buta-1,3-dienyl)-1H-indole (Ic-29)
6-(4-pyridin-2-yl-buta-1,3-dienyl)-1H-benzimidazole (Ic-30)
2-(4-naphthalen-2-yl-buta-1,3-dienyl)pyridine (Ic-31)
3-(4-pyridin-2-yl-buta-1,3-dienyl)quinoline (Ic-32)
6-(4-pyridin-2-yl-buta-1,3-dienyl)quinoline (Ic-33)
2-(4-benzofuran-5-yl-buta-1,3-dienyl)pyridine (Ic-34)
2-(4-benzofuran-6-yl-buta-1,3-dienyl)pyridine (Ic-35)
5-(4-pyridin-2-yl-buta-1,3-dienyl)-1H-indole (Ic-36)
2-(4-benzo[b]thiophen-5-yl-buta-1,3-dienyl)pyridine (Ic-37)
5-(4-pyridin-2-yl-buta-1,3-dienyl)benzothiazole (Ic-38)
2-[4-(2-nitrophenyl)buta-1,3-dienyl]pyridine (Ic-39)
2-[4-(4-nitrophenyl)buta-1,3-dienyl]pyridine (Ic-40)
2-[4-(4-fluorophenyl)buta-1,3-dienyl]pyridine (Ic-41)
2-[4-(4-chlorophenyl)buta-1,3-dienyl]pyridine (Ic-42)
2-[4-(3-fluorophenyl)buta-1,3-dienyl]pyridine (Ic-43)
2-[4-(4-methylsulfanylphenyl)buta-1,3-dienyl]pyridine (Ic-44)
N-[4-(4-pyridin-2-yl-buta-1,3-dienyl)phenyl]acetamide (Ic-45)
dimethyl-[4-(4-pyridin-2-yl-buta-1,3-dienyl)phenyl]amine (Ic-46)
1,4-bis-(2-pyridyl)-1,3-butadiene (Ic-48)
2-(4-pyridin-2-yl-buta-1,3-dienyl)quinoline (Ic-49)
1-(2-pyridyl)-4-(2-methylpyridin-6-yl)-1,3-butadiene (Ic-50)
1-(2-pyridyl)-4-(5-methylpyridin-2-yl)-1,3-butadiene (Ic-51)
1-(2-pyridyl)-4-(5-methoxypyridin-2-yl)-1,3-butadiene (Ic-52)
1-(2-pyridyl)-4-(4-methoxypyridin-2-yl)-1,3-butadiene (Ic-53)
1-(3-pyridyl)-4-(2-pyridyl)-1,3-butadiene (Ic-54)
1-(2-pyridyl)-4-(2-thiophen-2-yl-pyridin-5-yl)-1,3-butadiene (Ic-55)
1-(2-pyridyl)-4-(2-methylpyridin-5-yl)-1,3-butadiene (Ic-56)
1-(2-pyridyl)-4-(2-methoxypyridin-5-yl)-1,3-butadiene (Ic-57)
1-(2-pyridyl)-4-(2-chloropyridin-5-yl)-1,3-butadiene (Ic-58)
1-(2-pyridyl)-4-(4-pyridyl)-1,3-butadiene (Ic-59)
1-(2-pyridyl)-4-(2-chloropyridin-4-yl)-1,3-butadiene (Ic-60)
1-(2-pyridyl)-4-(2-methoxypyridin-4-yl)-1,3-butadiene (Ic-61)
1-(2-pyridyl)-4-(2-methylpyridin-4-yl)-1,3-butadiene (Ic-62)
5-(4-pyridin-2-yl-buta-1,3-dienyl)pyrimidine (Ic-63)
2-(4-pyridin-2-yl-buta-1,3-dienyl)-[1,3,5]triazine (Ic-64)
4-(4-pyridin-2-yl-buta-1,3-dienyl)pyrimidine (Ic-65)
2-(4-phenyl-buta-1,3-dienyl)quinoxaline (Ic-68)
2-(4-phenyl-buta-1,3-dienyl)quinoline (Ic-69)
3-(4-pyridin-3-yl-buta-1,3-dienyl)isoquinoline (Ic-70)
2-(3-methyl-4-phenyl-buta-1,3-dienyl)pyridine (Ic-71)
2-(3-pentyl-4-phenyl-buta-1,3-dienyl)pyridine (Ic-72)
2-(3-bromo-4-phenyl-buta-1,3-dienyl)pyridine (Ic-73)
2-(4-phenyl-penta-1,3-dienyl)pyridine (Ic-75)
2-phenyl-5-pyridin-2-yl-penta-2,4-diene nitrile (Ic-76)
5-phenyl-2-pyridin-2-yl-penta-2,4-diene nitrile (Ic-77)
2-(4-furan-2-yl-buta-1,3-dienyl)pyridine (Ic-78)
2-(4-furan-3-yl-buta-1,3-dienyl)pyridine (Ic-79)
2-(4-furan-3-yl-buta-1,3-dienyl)pyridine hydrochloride (Ic-80)
2-(4-thiophen-2-yl-buta-1,3-dienyl)pyridine (Ic-81)
2-(4-thiophen-3-yl-buta-1,3-dienyl)pyridine (Ic-82)
2-[4-(3-methylthiophen-2-yl)buta-1,3-dienyl]pyridine (Ic-83)
2-(4-thiazol-2-yl-buta-1,3-dienyl)pyridine (Ic-84)
2-[4-(5-methyl-3H-imidazol-4-yl)buta-1,3-dienyl]pyridine (Ic-85)
2-(4-isoxazol-4-yl-buta-1,3-dienyl)pyridine (Ic-86)
2-(4-isoxazol-3-yl-buta-1,3-dienyl)pyridine (Ic-87)
2-(4-oxazol-4-yl-buta-1,3-dienyl)pyridine (Ic-88)
2-[4-(1H-pyrazol-3-yl)buta-1,3-dienyl]pyridine (Ic-89)
2-[4-(1H-pyrrol-3-yl)buta-1,3-dienyl]pyridine (Ic-90)
2-[4-(1H-1,2,4-triazol-3-yl)buta-1,3-dienyl]pyridine (Ic-91)
2-(6-furan-3-yl-hexa-1,3,5-trienyl)pyridine (Ic-93)
2-(6-furan-2-yl-hexa-1,3,5-trienyl)pyridine (Ic-94)
2-(6-thiophen-3-yl-hexa-1,3,5-trienyl)pyridine (Ic-95)
2-(6-phenyl-hexa-1,3,5-trienyl)pyridine (Ic-96)
1,6-bis-(2-pyridyl)-1,3,5-hexatriene (Ic-97)
1-(2-pyridyl)-6-(3-pyridyl)-1,3,5-hexatriene (Ic-98)
1-(2-pyridyl)-6-(4-pyridyl)-1,3,5-hexatriene (Ic-102)
2-(6-thiazol-4-yl-hexa-1,3,5-trienyl)pyridine (Ic-103)

2-(6-thiophen-3-yl-hexa-1,3,5-trienyl)pyridine (Ic-104)
2-(6-isoxazol-4-yl-hexa-1,3,5-trienyl)pyridine (Ic-105)
2-(6-isoxazol-3-yl-hexa-1,3,5-trienyl)pyridine (Ic-106)
2-(6-oxazol-4-yl-hexa-1,3,5-trienyl)pyridine (Ic-107)
2-[6-(1H-pyrazol-3-yl)hexa-1,3,5-trienyl]pyridine (Ic-108)
2-[2-(2H-chromen-3-yl)vinyl]pyridine (Ic-110)
2-(4-phenyl-but-1-enyl)pyridine (Id-2)
2-styrylsulfanil-pyridine (Id-4) pyridin-2-yl-styrylamine (Id-5), and
(3-phenylallylidene)pyridin-2-yl-amine (Id-6).

Among them, more preferable compounds are as follows:
Ia-1, Ia-2, Ia-3, Ia-6, Ia-10, Ia-12, Ia-13, Ia-14, Ia-15, Ia-16, Ia-17, Ia-18, Ia-19, Ia-20, Ia-21, Ia-22. Ib-1, Ib-9, Ib-11, Ib-17, Ib-20, Ib-33, Ib-34, Ib-35, Ib-50, Ib-52, Ib-56, Ib-57, Ib-58, Ib-59, Ib-60, Ib-61, Ib-64, Ib-65, Ib-66, Ib-67, Ib-68, Ib-69, Ib-70, Ib-72, Ib-73, Ib-75, Ib-77, Ib-84, Ib-85, Ib-87, Ib-88, Ib-89, Ib-91, Ib-100, Ib-101, Ib-102, Ic-1, Ic-2, Ic-4, Ic-6, Ic-9, Ic-11, Ic-15, Ic-18, Ic-19, Ic-39, Ic-40, Ic-41, Ic-44, Ic-45, Ic-46, Ic-48, Ic-54, Ic-59, Ic-68, Ic-71, Ic-73, Ic-75, Ic-76, Ic-77, Ic-78, Ic-79, Ic-80, Ic-81, Ic-82, Ic-83, Ic-84, Ic-85, Ic-93, Ic-10, Id-2, and Id-4.

BEST MODE FOR CARRYING OUT THE INVENTION

Compounds (I) of the invention may be synthesized for example according to any one of Method A to D.

Method A: A-4+A-5→I

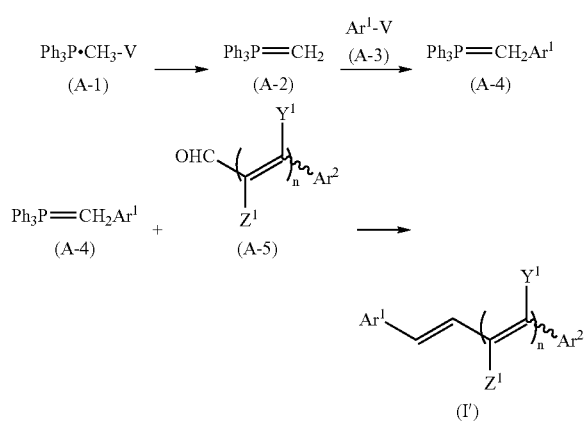

in which V is a halogen, and other symbols are as defined above.

The method is a reaction known as Wittig reaction. First, halide (A-3) as a starting material is reacted with Wittig reagent (A-2) that is prepared from methyl triphenyl phosphonium halide (A-1) and butyl lithium or the like, in an appropriate solvent to give A-4. Then, the compound (A-4) is reacted with aromatic aldehyde (A-5) to give intended vinyl derivative, diene derivative or triene derivative (I). The reaction may proceed at a temperature from room temperature to a reflux temperature of the solvent.

Method B: B-2+B-3→I

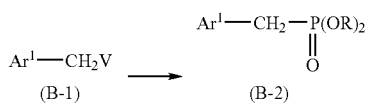

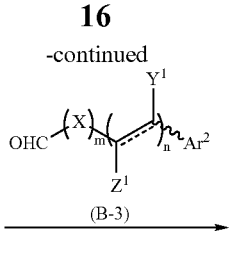

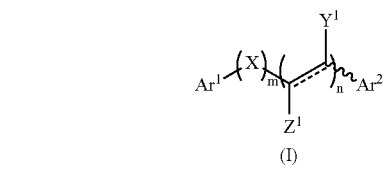

in which R is a lower alkyl, and the symbols are as defined above.

B-1 (for example benzyl halide) and a alkyl phosphite are reacted in the presence of a strong base such as a metallic sodium in an appropriate solvent such as benzene or toluene at a temperature from room temperature to a reflux temperature of the solvent to give B-2 (for example diethyl benzylphosphonate).

B-2 can be converted to compound (I) by reacting with one of various aldehydes (B-3) in the presence of a quaternary alkyl ammonium salt and an alkali hydroxide such as lithium hydroxide at a temperature from room temperature to a reflux temperature of the solvent. The reaction may proceed in a solvent such as methylene chloride, ethylene dichloride, or tetrahydrofuran.

Method C: C-1+C-2→I

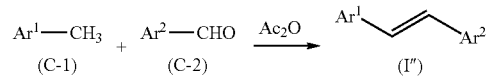

in which the symbols are as defined above.

The method is a reaction known as Perkin reaction. Specifically, a starting material (C-1) and aldehydes (C-2) are reacted in an appropriate solvent such as acetic anhydride at a temperature from room temperature to a reflux temperature of the solvent to give compound (I''), which is a compound wherein m in formula (I) is 0, n is 1, and $Y^1$ and $Z^1$ are H.

Method D: D-1+D-2→Ia

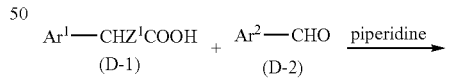

in which the symbols are as defined above.

Acetic acid derivative (D-1) and aldehydes (D-2) are reacted in the presence of a base such as piperidine at a temperature from room temperature to a reflux temperature of the solvent to give compound (I'''), which is a compound wherein m in formula (I) is 0, n is 1, and $Y^1$ is H. Benzene, toluene or pyridine may be used as a solvent.

The method of enhancing the expression of apoAI according to the invention activates a reverse cholesterol transport activity of HDL, an anti-inflammatory activity and an anticoagulant activity, or the like. As a result, the method of the invention are useful for preventing and/or treating dyslipidemia, arteriosclerotic diseases and various cardiovascular diseases associated with them, which are caused by decreased level of HDL in serum. "Dyslipidemia" specifically include conditions of lowered level of serum HDL, hypercholesteremia and hypertriglyceridemia; "arteriosclerotic diseases" specifically include arteriosclerosis, myocardial infarction, and cardiac incompetence; and "various cardiovascular diseases associated with the above diseases" include hyperuricemia, coronary artery diseases, ischaemic heart diseases, corneal opacity, cerebrovascular disease, and hereditary HDL deficiencies (Tangier disease, fish-eye disease).

When a compound of the invention is administered in the method according to the invention, pharmaceutical compositions therefor may be administered either orally or parenterally. For oral routes, the compositions may be formulated conventionally into usual dosage forms such as tablets, granules, powders, capsules, pills, solutions, syrups, buccals, sublinguals, or the like before administration. For parenteral administration, the compositions may be conventionally formulated into usual dosage forms such as injections, e.g., intramuscular or intravenous injections, suppositories; transdermal patches, inhalation, or the like.

An effective amount of a compound according to the invention may be admixed with various suitable pharmaceutical additives such as excipient, binding agent, wetting agent, disintegrating agent, lubricant, diluent, or the like to give pharmaceutical compositions, if necessary. In the case of injections, the ingredients are sterilized together with a suitable carrier to formulate the composition.

More specifically, the excipients include lactose, sucrose, glucose, starch, calcium carbonate, crystalline cellulose, or the like; the binding agents include methyl cellulose, carboxymethylcellulose, hydroxypropylcellulose, gelatine, polyvinyl pyrrolidone, or the like; the disintegrating agents include carboxymethylcellulose, sodium carboxymethyl cellulose, starch, sodium alginate, algae powder, sodium lauryl sulfate, or the like; the lubricants include talc, magnesium stearate or Macrogol, or the like. Base materials of the suppository may be for example cacao butter, Macrogol, methylcellulose, or the like. Solutions, emulsions or suspensions for injection may comprise a solubilizing agent, a suspending agent, an emulsifying agent, a stabilizing agent, a preserving agent, an isotonic agent, or the like as usually used. Compositions for oral administration may comprise a flavoring agent, an aromatic agent, or the like.

Dose or therapeutically effective amount of the compounds according to the invention for enhancing the expression of apoAI is preferably determined considering age and body weight of patients, sort and severity of diseases to be treated, route of administration, or the like. In the case of oral administration to an adult, the dose range is usually 1 to 100 mg/kg/day, preferably 5 to 30 mg/kg/day. In the case of parenteral administration, the dose differs largely depending on the route of administration, but the dose range is usually 0.1 to 10 mg/kg/day, preferably 1 to 5 mg/kg/day. The dosage unit may be administered to a subject once or several times per day.

Following examples and experiment are presented for purpose of further illustration of the invention, and they are not intended to limit the scope of the invention in any respect.

EXAMPLES

Reference 1
3-(4-Ethoxycarbonylpropoxy)benzaldehyde
(compound C1)

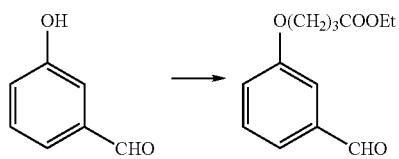

A suspension of 3-hydroxybenzaldehyde (1.0 g, 8.19 mmol), ethyl 4-bromobutyrate (1.76 g, 9.01 mmol), potassium carbonate (1.36 g, 9.83 mmol), and dimethylformamide (20 ml) was stirred at room temperature for 32 hours. To the reaction mixture were added ethyl 4-bromobutyrate (1.36 g, 4.09 mmol) and potassium carbonate (0.594 g, 4.30 mmol), and then the mixture was further stirred at 50° C. for 5 hours. After water was added to the reaction, the mixture was extracted with ether, and the extract was washed with water. The solvent was removed in vacuo. The residue was subjected to silica gel chromatography using toluene-ethyl acetate (9:1) as eluent to give compound C1 (2.10 g) as pale yellow oil as a mixture containing a small amount of ethyl 4-bromobutyrate, which was used in the subsequent reaction.

NMR (CDCl$_3$): 1.26 (3H, t, J=7.2), 2.10-2.22 (2H, m), 2.53 (2H, t, J=7.2), 4.10 (2H, t, J=6.3), 4.16 (2H, q, J=7.2), 7.15-7.19 (1H, m), 7.37-7.38 (1H, m), 7.43-7.47 (2H, m), 9.98 (1H, s).

Reference 2 Diethyl pyridin-2-yl-methyl
phosphonate (compound B1)

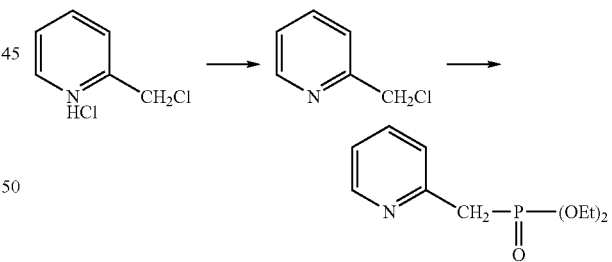

2-Chloromethylpyridine hydrochloride (75.7 g, 0.46 mol) was dissolved in water (100 ml), and the solution was made alkaline by adding a 96% aqueous solution of sodium hydroxide (19.23 g, 0.46 mol) in water (200 ml). The mixture was extracted with ether, and the extract was dried over anhydrous magnesium sulfate, after which the solvent was removed in vacuo. The residue was purified by vacuum distillation to give 2-chloromethylpyridine (52.72 g, 89.6%) as pale red oil. Boiling point: 76-78° C./2133 Pa To a solution of ethyl phosphite (57.07 g, 0.413 mol) in benzene (470 ml) was added metallic sodium (9.50 g, 0.413 mol), and the mixture was heated at reflux for 4 hours, followed by adding dropwise the solution of 2-chloromethylpyridine (52.72 g, 0.413 mol) in benzene (350 ml) as described above over 15 minutes at the same temperature. After heated at reflux for 2 hours, the reaction was allowed to cool to room temperature, and the benzene solution was washed with water, dried over anhydrous magnesium sulfate, and evaporated in vacuo. The residue was subjected to silica gel chromatography using ethyl acetate-methanol (19:1) as eluent to give B1 (66.25 g, 69.9%) as oil.

Reference 3 1-Methoxymethylpyrrol-2-aldehyde (compound B2)

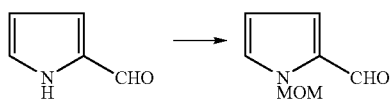

To a solution of pyrrol-2-carbaldehyde (951 m g, 10.00 mmol) in dimethylsulfoxide (20 ml) were added a 4M aqueous sodium hydroxide (2.5 ml, 10 mmol) and methoxymethyl chloride (0.84 ml, 11.00 mmol) sequentially, and the mixture was stirred at room temperature for 16 hours. The reaction mixture was extracted with ether, and the extract was washed with water and saturated brine, dried over anhydrous magnesium sulfate, and evaporated in vacuo. The residue was subjected to silica gel chromatography using chloroform-acetonitrile (95:5) as eluent to give B2 (557 m g, 40%) as oil.

Reference 4 Methyl 2-hydroxy-5-methoxybenzoate (compound A1)

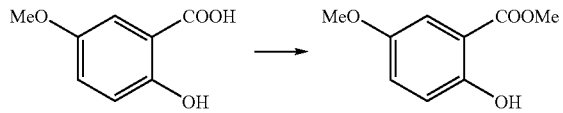

To a solution of 2-hydroxy-5-methoxybenzoic acid (6.0 g, 35.68 mmol) in dimethylformamide (80 ml) were added sodium hydrogen carbonate (3.15 g, 37.46 mmol) and methyl iodide (2.33 ml, 37.46 mmol), and the mixture was stirred at 80° C. for 3 hours. After an ice water was added to the reaction, the mixture was extracted with ether, and the extract was washed with water and saturated brine, and dried over anhydrous magnesium sulfate. The solvent was removed in vacuo to give A1 (5.38 g, 82.8%) as brown oil.

Reference 5 1-(2-Hydroxy-5-methoxyphenyl)-2-(triphenyl-phosphoridene)ethanone (compound A2)

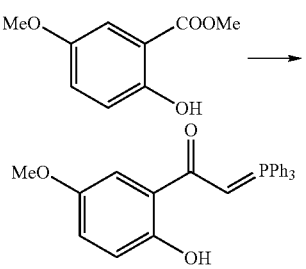

To sodium hydride (60%, 305 m g, 7.62 mmol) rinsed with hexane was added a solution of methyl benzoate A1 described in Reference 4 (500 m g, 2.74 mmol) in dimethylformamide (20 ml), and the mixture was stirred at 80° C. for 45 minutes. After cooled to below 20° C., methyltriphenylphosphonium bromide (1.96 g, 5.49 mmol) was added dropwise, and the mixture was stirred at room temperature for 30 minutes and then at 80° C. for 22 hours. After an ice water was added to the reaction, the mixture was extracted with ether, and the extract was washed with water and saturated brine, and dried over anhydrous magnesium sulfate. The solvent was removed in vacuo. The residue was subjected to silica gel chromatography using ethyl acetate-hexane (1:1) as eluent to give compound A2 (407 m g, 34.8%) as pale yellow oil.

NMR (CDCl$_3$): 3.77 (3H, s), 6.81 (1H, d, J=9.0), 6.89 (1H, dd, J=3.0, 9.0), 7.23 (1H, d, J=3.0), 7.47-7.74 (16H, m)

Reference 6 4-Methylcinnamaldehyde (compound B3)

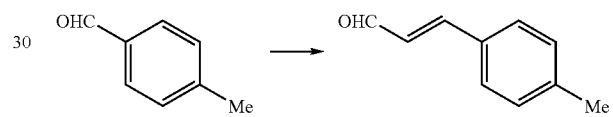

To a solution of sodium hydroxide (2.0 g, 50 mmol) in a mixture of ethanol (12 ml) and water (24 ml) was added p-tolualdehyde (9.0 g, 74.9 mmol), and the mixture was stirred at 0° C. for 15 minutes, and then 40% acetaldehyde (20 g, 181.6 mmol) was added dropwise over 4 hours. After cooled to 0° C., the reaction mixture was neutralized with 20% acetic acid. Then, the mixture was extracted with ether, and the extract was washed with saturated brine, dried over anhydrous magnesium sulfate, and evaporated in vacuo. The residue was subjected to silica gel chromatography using isopropylether-hexane (1:2) as eluent to give B3 (6.03 g, 55.1%) as oil.

Reference 7 3-(3-Thienyl)acrolein (compound B4)

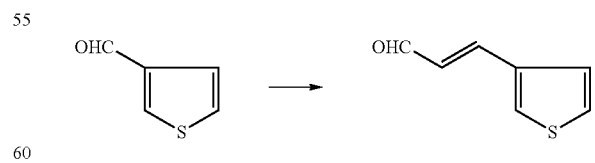

To a solution of sodium hydroxide (1.0 g, 25 mmol) in a mixture of ethanol (6 ml) and water (12 ml) was added thiophen-3-carbaldehyde (4.5 g, 40.1 mmol), and the mixture was stirred at 0° C. for 10 minute. To the mixture was dropwise added 40% acetaldehyde (10 g, 90.8 mmol) over 3 hours at the same temperature, and the mixture was further stirred for 30 minutes. The reaction mixture was treated in a similar manner to that in Reference 6 to give compound B4 (3.58 g, 64.6%) as oil.

Example 1

2-[2-(4-chlorophenyl) vinyl]quinoxaline (Ib-65)

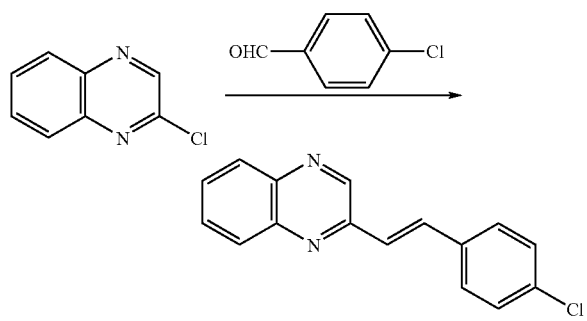

Method A: To a solution of methyl triphenyl phosphonium bromide (11.86 g, 33.2 mmol) in tetrahydrofuran (100 ml) was added dropwise n-butyl lithium (a 1.66 M solution in hexane, 20 ml, 33.2 mmol) at room temperature. The mixture was stirred for 30 minutes at the same temperature, and then heated at reflux for an hour. After the reaction mixture was cooled to room temperature, 2-chloroquinoxaline (2.73 g, 16.6 mmol; U.S. Pat. No. 2,573,870: C.A., 45, 4274 (1951)) was added, and the mixture was stirred at room temperature for 2 hours. Then, 4-chlorobenzaldehyde (2.33 g, 16.6 mmol) was added, and the mixture was stirred for 30 minutes. After the insoluble materials were removed by filtration, and washed with tetrahydrofuran, the filtrate and the washing were combined, and concentrated in vacuo. The residue was subjected to silica gel chromatography using chloroform-acetone (19:1) as eluent, and then recrystallized from ethyl acetate to give Ib-65 (2.70 g, 61%) as yellow crystal.

Example 2

4-(2-Quinoxaline-2-yl-vinyl)benzoic acid (Ib-59)

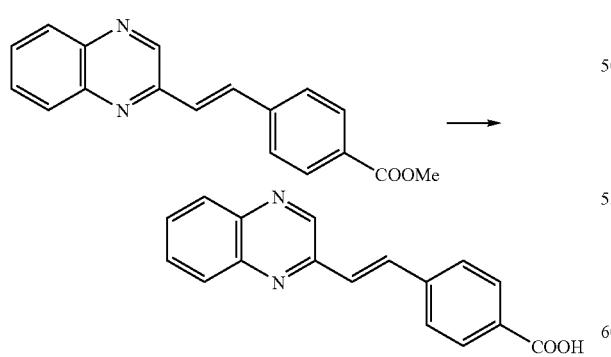

To a solution of Ib-58 (410 m g, 1.40 mmol) as obtained in a similar manner to Example 1 in methanol (4 ml) and tetrahydrofuran (4 ml) was added 1M aqueous sodium hydroxide (3 ml, 3.00 mmol), and the mixture was stirred at room temperature for 2 hours. Water was added, and the mixture was washed with ethyl acetate. The aqueous alkaline layer was made acidic with hydrochloric acid, and the precipitated crystals were collected by filtration. Recrystallization from methanol gave Ib-59 (336 m g, 86%).

Example 3

4-(2-Quinoxaline-2-ylvinyl)phenylamine (Ib-69)

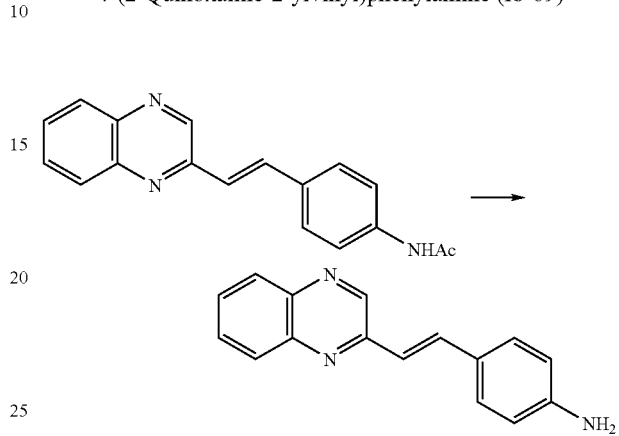

To a solution of N-[4-(2-quinoxaline-2-ylvinyl)phenyl]acetamide (Ib-70, 289 m g, 1.00 mmol) as obtained in a similar manner to Example 1 in ethanol (1.6 ml) and water (1.6 ml) was added 1M potassium hydroxide (0.80 g, 14.26 mmol), and the mixture was heated to reflux for 4 hours. The reaction was neutralized by adding acetic acid under ice cooling, and the precipitated crystals were collected by filtration, and recrystallization from methanol gave Ib-69 (107 m g, 43%).

Example 4

Ethyl 4-[3-(2-quinoline-2-yl-vinyl)phenoxy]butanoate (Ib-88)

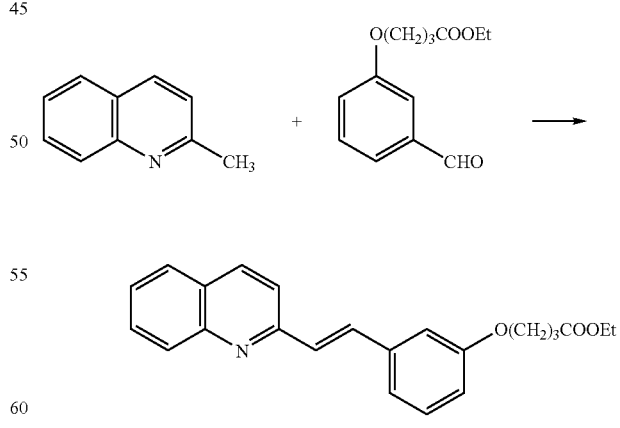

Method C: To quinaldine (1.00 g, 6.95 mmol) were added compound C1 (1.80 g, 7.65 mmol) as described in Reference 1 and acetic anhydride (1.31 ml, 13.9 mmol), and the mixture was stirred at 150° C. for 5 hours. The solvent was removed in vacuo, and the residue was subjected to silica gel chromatography using toluene-ethyl acetate (9:1) as eluent. Recrystallization from ethyl acetate-hexane gave Ib-88 (1.09 g, 43.4%) as colorless crystal.

Example 5

4-[3-(2-quinoline-2-yl-vinyl)phenoxy]butanoic acid (Ib-89)

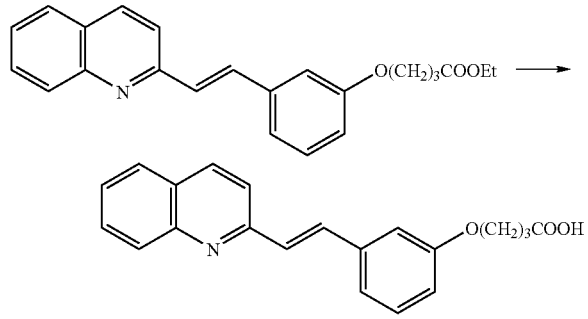

To a solution of Ib-88 (100 m g, 0.277 mmol) prepared in Example 41 in methanol (1 ml) and tetrahydrofuran (1 ml) was added 1N aqueous potassium hydroxide (0.66 ml, 0.66 mmol), and the mixture was stirred at room temperature for 25 hours, after which the reaction was concentrated in vacuo. After ice water was added to the residue, the mixture was made weak acid by adding 1N aqueous hydrochloric acid, and extracted with ethyl acetate. The extract was washed with water and saturated brine, and dried over anhydrous magnesium sulfate. The solvent was removed in vacuo to give the residue, which was recrystallized from acetone-isopropylether to give Ib-89 (69 m g, 75%).

Example 6

2-Styryl-pyridine (Ib-1)

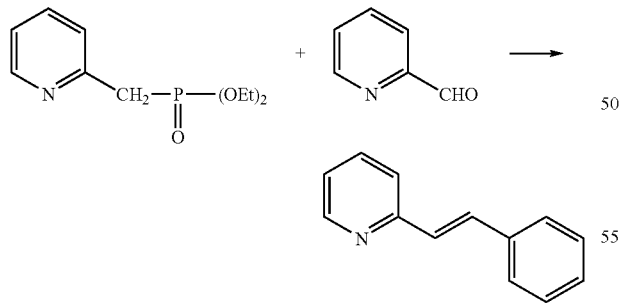

Method B: To a solution of compound B1 (458 m g, 2.00 mmol) in dichloromethane (2 ml) were added benzaldehyde (212 m g, 2.00 mmol), 48% aqueous sodium hydroxide (1.2 ml) and tetrabutylammonium iodide (60 m g, 0.16 mmol), and the mixture was stirred at room temperature for 1 hour. After water was added to the reaction, the mixture was extracted with ether, and the extract was washed with water and saturated brine, dried over anhydrous magnesium sulfate, and evaporated in vacuo. The residue was recrystallized from isopropylether to give Ib-1 (242 m g, 67%).

Example 7

2-(2-Thiophen-3-yl-vinyl)pyridine (Ib-52)

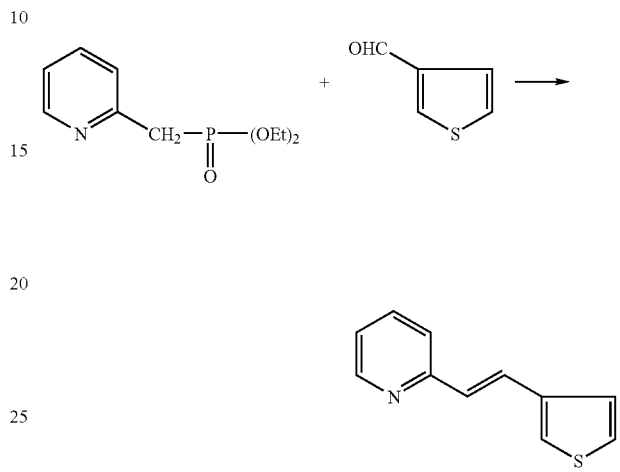

Method B: To a solution of compound B1 (5.339 g, 23.29 mmol) described in Reference 2 in dichloromethane (23 ml) were added thiophen-3-carbaldehyde (2.612 g, 23.29 mmol), 48% aqueous sodium hydroxide (14.0 ml) and tetrabutylammonium iodide (0.700 g, 1.90 mmol), and the mixture was stirred at room temperature for 3 hours. The reaction was treated in a similar manner to Example 7. The residue was subjected to silica gel chromatography using chloroform-acetonitrile (19:1), and recrystallization from acetone-isopropylether gave Ib-52 (2.67 g, 61.2%).

Method D:

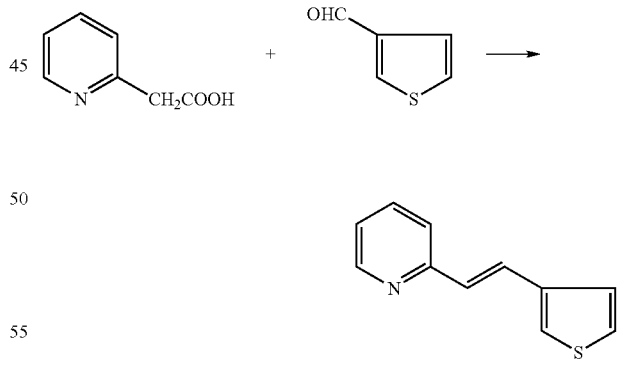

To a solution of 2-pyridylacetic acid hydrochloride (868 m g, 5.00 mmol) and thiophen-3-carbaldehyde (841 m g, 7.50 mmol) in pyridine (7.5 ml) was added piperidine (0.05 ml, 0.51 mmol), and the mixture was heated at reflux for 20 hours. After the solvent was removed from the reaction in vacuo, the residue was extracted with ethyl acetate, and the extract was washed sequentially with 1M aqueous sodium hydroxide, water and saturated brine, and dried over anhydrous magnesium sulfate. The residue was subjected to silica gel chromatography using chloroform-acetonitrile (19:1). Recrystallization from acetone-isopropylether gave Ib-52 (198 m g, 21.2%).

Example 8

2-(4-phenylbutan-1,3-dienyl)quinoxaline (Ic-68)

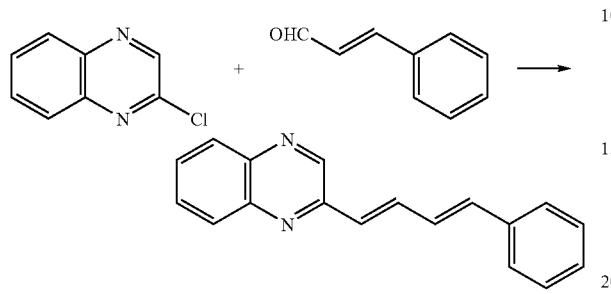

Method A: To a solution of methyltriphenylphosphonium bromide (2.20 g, 6.16 mmol) in tetrahydrofuran (10 ml) was added n-butyl lithium (1.66 M solution in hexane, 4 ml, 6.16 mmol) at room temperature in a nitrogen atmosphere. After stirred for 40 minutes, 2-chloroquinoxaline (0.507 g, 3.08 mmol) was added, and the mixture was stirred at room temperature for 2 hours. Then, cinnamaldehyde (0.407 g, 3.08 mmol) was added, and the mixture was stirred for an hour. The reaction mixture was subjected to silica gel chromatography using ethyl acetate-hexane (1:2) as eluent. Recrystallization from ethyl acetate-hexane gave Ic-68 (0.148 g, 18.6%).

Example 9

2-(4-Phenylbutan-1,3-dienyl)pyridine (Ic-1)

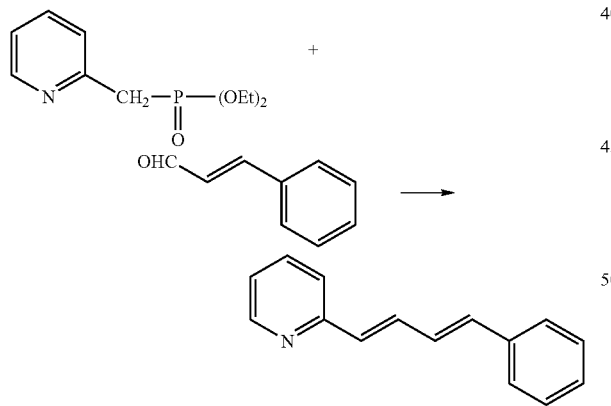

Method B: A solution of compound B1 (10.25 g, 44.7 mmol) described in Reference 2 and cinnamaldehyde (5.91 g, 44.7 mmol) in methylene chloride (6 ml) was dropwise added to a solution of 48% aqueous sodium hydroxide (26 ml) and tetrabutylammonium iodide (0.9 g, 2.4 mmol) in methylene chloride (47 ml) over 10 minutes at room temperature, and the mixture was stirred for 15 minutes. Then, the mixture was heated at reflux for an hour. After ice water was added, the mixture was extracted with toluene, and the extract was washed with water, dried over anhydrous magnesium sulfate, and evaporated in vacuo. The residue was subjected to silica gel chromatography using chloroform-hexane (4:1) as eluent. Recrystallization from ethyl acetate-hexane gave Ic-1 (3.95 g, 42.6%).

Example 10

2-(4-p-tolyl-buta-1,3-dienyl)-pyridine (Ic-6)

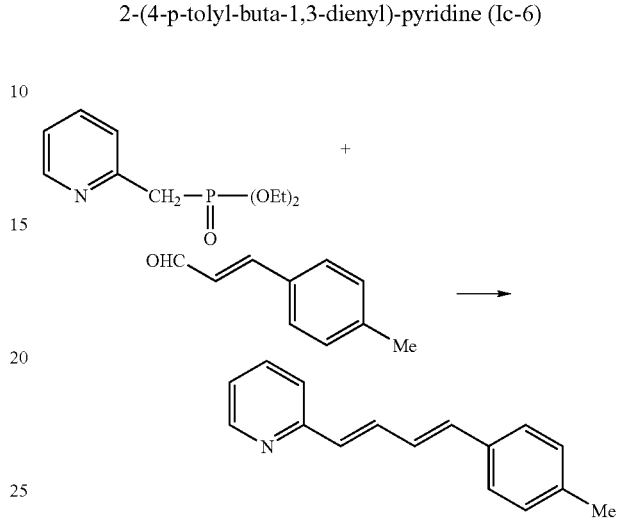

Method B: Compound B1 (8.251 g, 36.0 mmol) described in Reference 2, Compound B3 (5.262 g, 36.0 mmol) described in Reference 6, tetrabutylammonium iodide (1.08 g, 2.9 mmol) and 48% aqueous sodium hydroxide (21.6 ml) were stirred in dichloromethane (44 ml) at room temperature for an hour. The reaction was treated in a similar manner to Example 9, and the residue was subjected to silica gel chromatography using ethyl acetate-hexane (1:2) as eluent. Recrystallizing from ethyl acetate-hexane gave Ic-6 (2.28 g, 28.6%).

Example 11

2-(4-Thiophen-3-yl-buta-1,3-dienyl)pyridine (Ic-82)

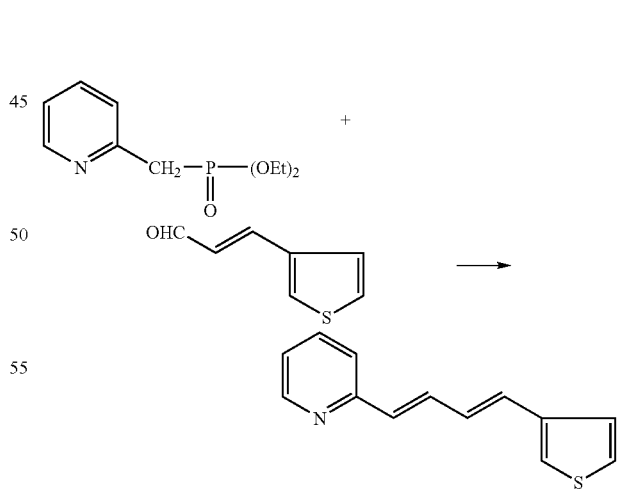

Method B: Compound B1 (3.577 g, 15.6 mmol) described in Reference 2, the aldehyde (B4, 2.156 g, 15.6 mmol) described in Reference 7, tetrabutylammonium iodide (0.47 g, 1.27 mmol) and 48% aqueous sodium hydroxide (9.5 ml) were heated at reflux in dichloromethane (19.6 ml) for an hour. The reaction was treated in a similar manner to Example 9, and the residue was subjected to silica gel chromatography using toluene-hexane (9:1) as eluent.
Recrystallizing from ethyl acetate-hexane gave Ic-82 (1.453 g, 43.7%).
In a similar manner, other compounds were prepared, of which chemical structures are shown in the following tables.
TABLE 1
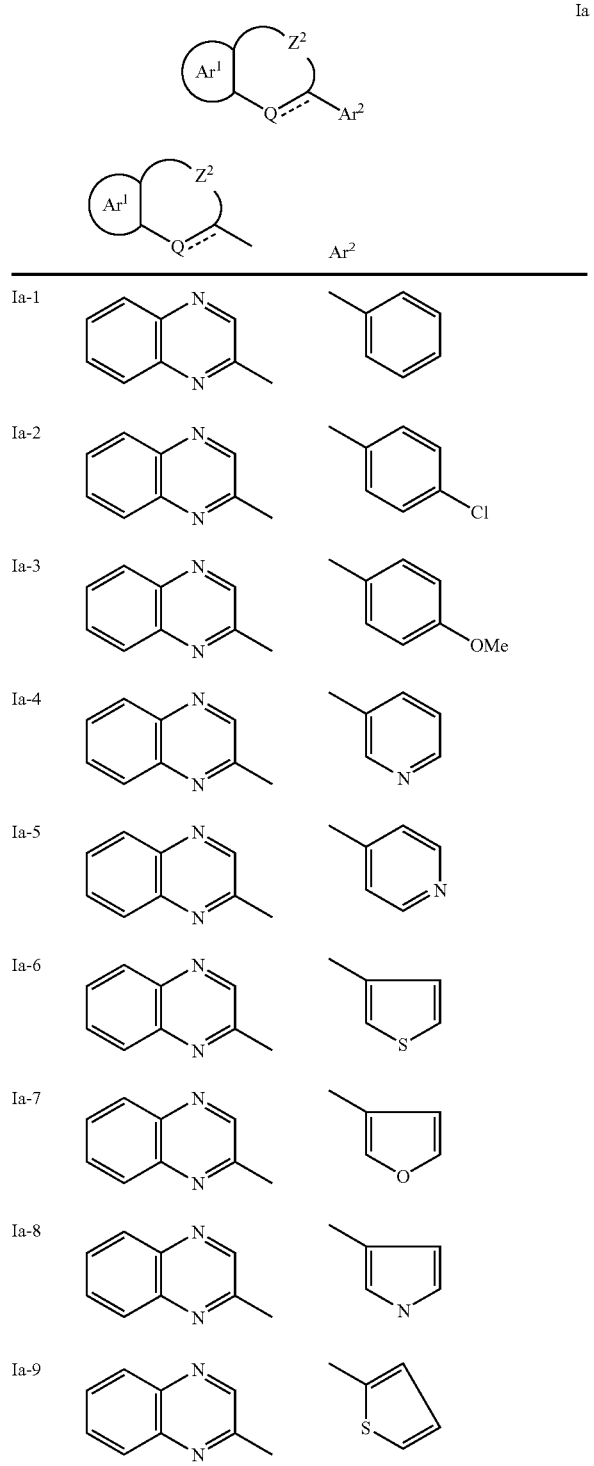
TABLE 1-continued
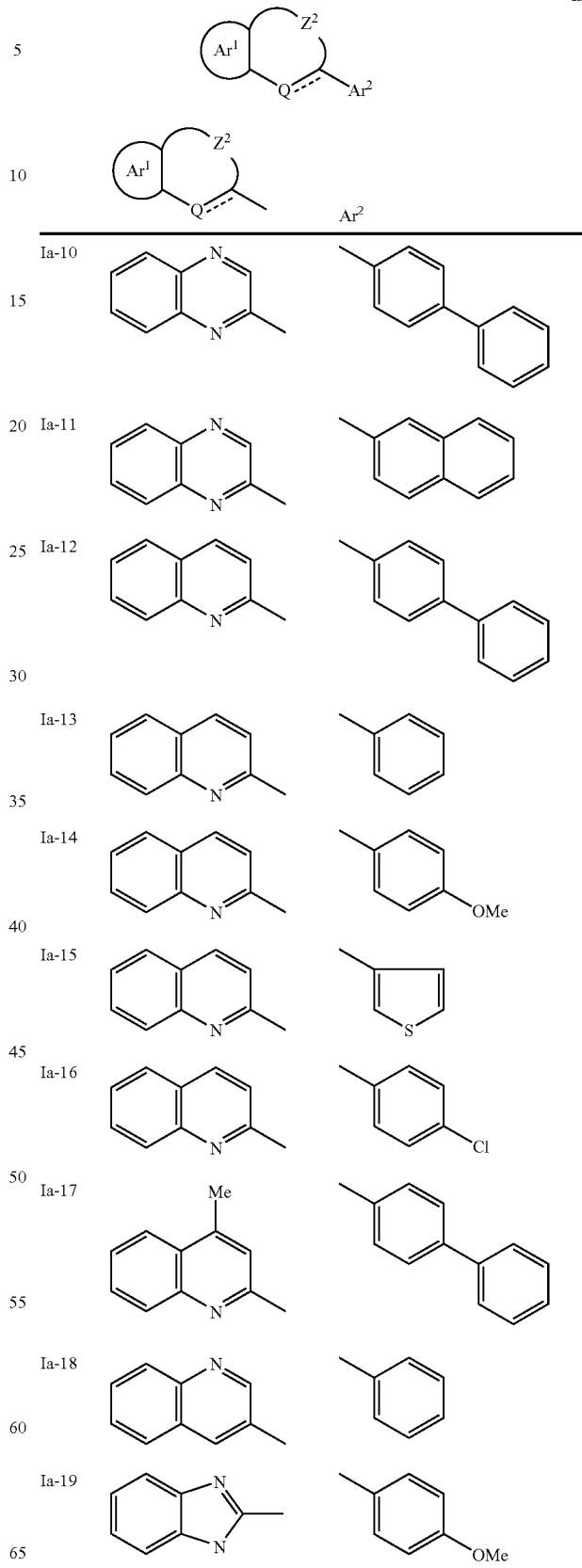

TABLE 1-continued

Ia

[Structures showing Ar¹ and Ar² with Z² and Q linkages]

| | Ar¹ | Ar² |
|---|---|---|
| Ia-20 | 2-methylbenzothiazole | phenyl |
| Ia-21 | 2-methylbenzothiazole | 2-methylbenzothiazole |
| Ia-22 | 2-methylbenzoxazole | 4-methoxyphenyl |

TABLE 2

Ar¹—CH=CH—Ar² (salt)    Ib

| | Ar¹ | Ar² |
|---|---|---|
| Ib-1 | 2-pyridyl | phenyl |
| Ib-2 | 2-pyridyl | 4-Me-phenyl |
| Ib-3 | 2-pyridyl | 4-CO₂Me-phenyl |
| Ib-4 | 2-pyridyl | 4-CO₂H-phenyl |
| Ib-5 | 2-pyridyl | 4-CN-phenyl |
| Ib-6 | 2-pyridyl | 4-phenyl-phenyl (biphenyl) |
| Ib-7 | 2-pyridyl | 4-F-phenyl |
| Ib-8 (MeI) | 2-pyridyl | 4-NHAc-phenyl |
| Ib-9 | 2-pyridyl | 4-CF₃-phenyl |
| Ib-10 (MeI) | 2-pyridyl | 4-NMe₂-phenyl |
| Ib-11 | 2-pyridyl | 2-HO-phenyl |
| Ib-12 | 2-pyridyl | 4-OMe-phenyl |
| Ib-13 | 2-pyridyl | benzo[1,3]dioxole |
| Ib-14 | 2-pyridyl | 2,3-dihydro-1,4-benzodioxine |
| Ib-15 (2HCl) | 2-pyridyl | 4-NHNH₂-phenyl |
| Ib-16 | 2-pyridyl | benzimidazole |
| Ib-17 | 2-pyridyl | 2-naphthyl |
| Ib-18 (MeI) | 2-pyridyl | 1-naphthyl |

TABLE 2-continued
| | Ar¹ | Ar² |
|---|---|---|
| Ib-19 | 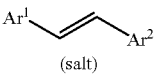 | 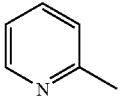 |
| Ib-20 | 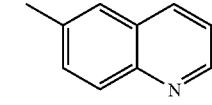 | 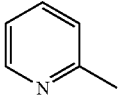 |
| Ib-21 | 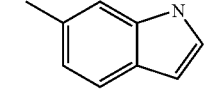 | 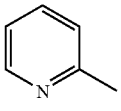 |
| Ib-22 | 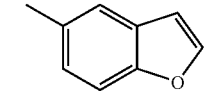 | 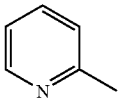 |
| Ib-23 | 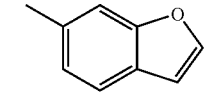 | 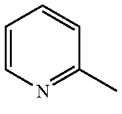 |
| Ib-24 | 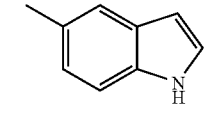 | 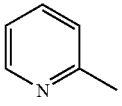 |
| Ib-25 | 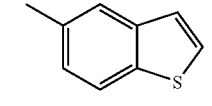 | 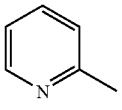 |
| Ib-26 | 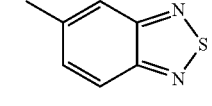 | 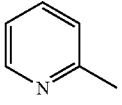 |
| Ib-27 | 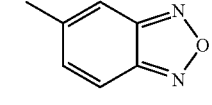 | 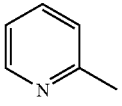 |
| Ib-28 | 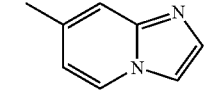 | 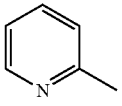 |
| Ib-29 | 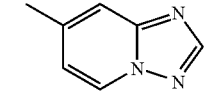 | 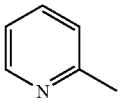 |
| Ib-30 | 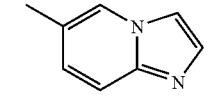 | 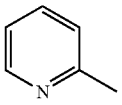 |
TABLE 2-continued
| | Ar¹ | Ar² |
|---|---|---|
| Ib-31 | 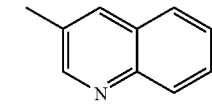 | 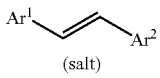 |
| Ib-32 | 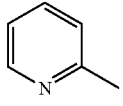 | 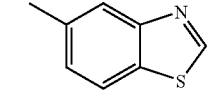 |
| Ib-33 | 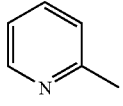 | 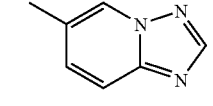 |
| Ib-34 | 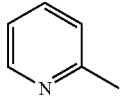 | 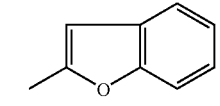 |
| Ib-35 | 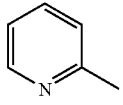 | 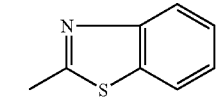 |
| Ib-36 | 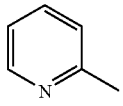 | 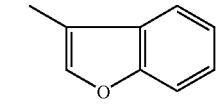 |
TABLE 3
| | Ar¹ | Ar² |
|---|---|---|
| Ib-37 | 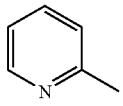 | 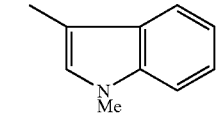 |
| Ib-38 | 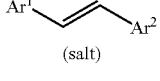 | 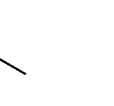 |
| Ib-39 | 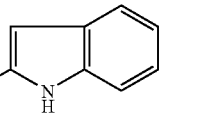 | 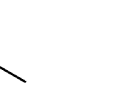 |
| Ib-40 | 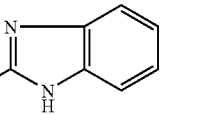 | 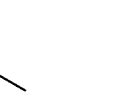 |

TABLE 3-continued
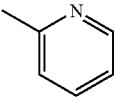

TABLE 3-continued $$\text{Ar}^1\text{—CH=CH—Ar}^2 \quad \text{(salt)} \qquad \text{Ib}$$

| | Ar¹ | Ar² |
|---|---|---|
| Ib-64 | 2-methylquinoxalin-3-yl | 4-fluorophenyl |
| Ib-65 | 2-methylquinoxalin-3-yl | 4-chlorophenyl |
| Ib-66 | 2-methylquinoxalin-3-yl | 4-bromophenyl |
| Ib-67 | 2-methylquinoxalin-3-yl | 4-methoxyphenyl |
| Ib-68 | 2-methylquinoxalin-3-yl | 4-hydroxyphenyl |
| Ib-69 | 2-methylquinoxalin-3-yl | 4-aminophenyl |
| Ib-70 | 2-methylquinoxalin-3-yl | 4-acetamidophenyl |
| Ib-71 | 2-methylquinoxalin-3-yl | 4-(dimethylamino)phenyl |
| Ib-72 | 2-methylquinoxalin-3-yl | 4-phenoxyphenyl |

TABLE 4

$$\text{Ar}^1\text{—C(Z}^1\text{)=CH—Ar}^2 \qquad \text{Ib}$$

| | Ar¹ | Z¹ | Ar² |
|---|---|---|---|
| Ib-73 | 2-methylquinoxalin-3-yl | H | 2-furyl |
| Ib-74 | 2-methylquinoxalin-3-yl | H | 2-thienyl |
| Ib-75 | 2-methylquinoxalin-3-yl | H | 3-furyl |
| Ib-76 | 2-methylquinoxalin-3-yl | H | 5-methylthiazol-2-yl |
| Ib-77 | 2-methylquinoxalin-3-yl | H | 3-thienyl |

TABLE 4-continued $$\underset{Z^1}{\overset{Ar^1}{\diagdown}}\!\!=\!\!\overset{Ar^2}{\diagup} \quad Ib$$

| | Ar¹ | Z¹ | Ar² |
|---|---|---|---|
| Ib-78 | 3-methylquinoxaline | H | 1H-pyrrol-3-yl |
| Ib-79 | 3-methylquinoxaline | H | 1H-1,2,3-triazol-4-yl |
| Ib-80 | 2-methylbenzoxazole | H | 4-(NMe₂)phenyl |
| Ib-81 | 2-methylbenzoxazole | H | 4-methylphenyl |
| Ib-82 | 2-methylbenzoxazole | H | 4-(CO₂H)phenyl |
| Ib-83 | 2-methylbenzoxazole | H | 1-methyl-5-methyl-pyrrol-2-yl |
| Ib-84 | 2-methylbenzoxazole | H | pyridin-2-yl |
| Ib-85 | 2-methylbenzothiazole | H | 4-(NMe₂)phenyl |
| Ib-86 | 2-methylbenzothiazole | H | 4-(CN)phenyl |
| Ib-87 | 2-methylbenzothiazole | H | thiophen-3-yl |
| Ib-88 | 2-methylquinoline | H | 3-(O(CH₂)₃CO₂Et)phenyl |
| Ib-89 | 2-methylquinoline | H | 3-(O(CH₂)₃CO₂H)phenyl |

TABLE 4-continued
| | Ar¹ | Z¹ | Ar² |
|---|---|---|---|
| Ib-90 | 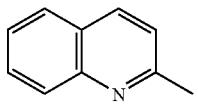 | H |  |
| Ib-91 | 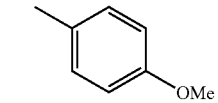 | H | 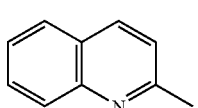 |
| Ib-92 |  | H |  |
| Ib-93 | 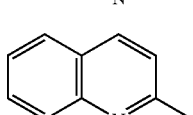 | H |  |
| Ib-94 | 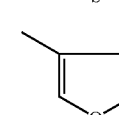 | H | 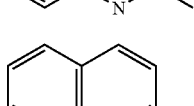 |
| Ib-95 |  | H | 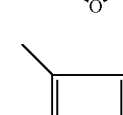 |
| Ib-96 | 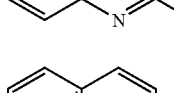 | H |  |
| Ib-97 | 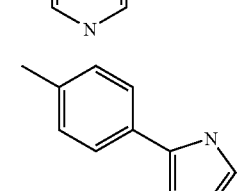 | H | 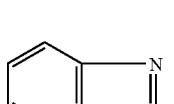 |
| Ib-98 |  | H | 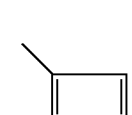 |
| Ib-99 | 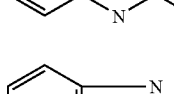 | H |  |
| Ib-100 | 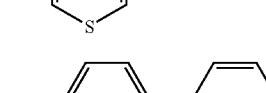 | H | 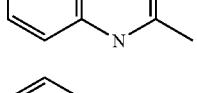 |
| Ib-101 |  | CN | 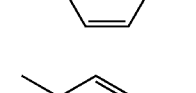 |

TABLE 4-continued

| | Ar¹ | Z¹ | Ar² | Ib |
|---|---|---|---|---|
| Ib-102 | phenyl-(5-methyl-1,3,4-oxadiazol-2-yl) | H | 3-pyridyl | |
| Ib-103 | (3-methoxyphenyl)-(5-methyl-1,3,4-oxadiazol-2-yl) | H | 3-pyridyl | |

TABLE 5

| | Ar¹ | Ar² | Ic |
|---|---|---|---|
| Ic-1 | 2-pyridyl | phenyl | |
| Ic-2 | 2-pyridyl | 2-methylphenyl | |
| Ic-3 | 2-pyridyl | 2,4-dimethylphenyl | |
| Ic-4 | 2-pyridyl | 3-methylphenyl | |
| Ic-5 | 2-pyridyl | 3,5-dimethylphenyl | |
| Ic-6 | 2-pyridyl | 4-methylphenyl | |
| Ic-7 | 2-pyridyl | 3,4-dimethylphenyl | |
| Ic-8 | 2-pyridyl | 2,4,6-trimethylphenyl | |
| Ic-9 | 2-pyridyl | 4-trifluoromethylphenyl | |
| Ic-10 | 2-pyridyl | 3-trifluoromethylphenyl | |
| Ic-11 | 2-pyridyl | 4-methoxyphenyl | |
| Ic-12 | 2-pyridyl | 3-methoxyphenyl | |
| Ic-13 | 2-pyridyl | 3,4-dimethoxyphenyl | |
| Ic-14 | 2-pyridyl | 3,4,5-trimethoxyphenyl | |

TABLE 5-continued

Structural formulas for compounds Ic-15 through Ic-36, each showing Ar¹ (2-pyridyl) and Ar² substituents connected via a butadiene linker:

- Ic-15: Ar² = 4-methoxy-3-methylphenyl
- Ic-16: Ar² = 2,6-dimethyl-4-hydroxyphenyl (with Me, OH, Me)
- Ic-17: Ar² = 3-methoxy-4-acetoxyphenyl (OMe, OAc)
- Ic-18: Ar² = 3-methoxy-4-acetoxyphenyl (OMe, OAc)
- Ic-19: Ar² = 3-methoxy-4-hydroxyphenyl (OMe, OH)
- Ic-20: Ar² = benzo[1,3]dioxol-5-yl
- Ic-21: Ar² = 4-methylbenzo[1,3]dioxol-6-yl (Me substituted)
- Ic-22: Ar² = 2,3-dihydro-1,4-benzodioxin-6-yl
- Ic-23: Ar² = 2,1,3-benzothiadiazol-5-yl
- Ic-24: Ar² = 2,1,3-benzoxadiazol-5-yl
- Ic-25: Ar² = imidazo[1,2-a]pyridin-6-yl
- Ic-26: Ar² = [1,2,4]triazolo[1,5-a]pyridin-6-yl
- Ic-27: Ar² = imidazo[1,2-a]pyridin-6-yl
- Ic-28: Ar² = [1,2,4]triazolo[1,5-a]pyridin-6-yl
- Ic-29: Ar² = 1H-indol-6-yl
- Ic-30: Ar² = 1H-benzimidazol-5-yl
- Ic-31: Ar² = naphthalen-2-yl
- Ic-32: Ar² = quinolin-3-yl
- Ic-33: Ar² = quinolin-6-yl
- Ic-34: Ar² = benzofuran-5-yl
- Ic-35: Ar² = benzofuran-6-yl
- Ic-36: Ar² = 1H-indol-5-yl

TABLE 6

Ic structure: Ar¹–CH=CH–C(Z¹)=CH–Ar²

| | Ar¹ | Z¹ | Ar² |
|---|---|---|---|
| Ic-37 | 2-pyridyl | H | benzothiophen-5-yl |
| Ic-38 | 2-pyridyl | H | benzothiazol-5-yl |
| Ic-39 | 2-pyridyl | H | 2-nitrophenyl |
| Ic-40 | 2-pyridyl | H | 4-nitrophenyl |
| Ic-41 | 2-pyridyl | H | 4-fluorophenyl |
| Ic-42 | 2-pyridyl | H | 4-chlorophenyl |
| Ic-43 | 2-pyridyl | H | 3-fluorophenyl |
| Ic-44 | 2-pyridyl | H | 4-(SMe)phenyl |
| Ic-45 | 2-pyridyl | H | 4-(NHAc)phenyl |
| Ic-46 | 2-pyridyl | H | 4-(NMe₂)phenyl |
| Ic-47 | 2-pyridyl (MeI) | H | 4-(NMe₂)phenyl |
| Ic-48 | 2-pyridyl | H | 6-methylpyridin-2-yl |
| Ic-49 | 2-pyridyl | H | 2-methylquinolin-... |
| Ic-50 | 2-pyridyl | H | 2,6-dimethylpyridin-3-yl |
| Ic-51 | 2-pyridyl | H | 2-methyl-5-methylpyridin-... |
| Ic-52 | 2-pyridyl | H | 6-methyl-3-methoxypyridinyl |
| Ic-53 | 2-pyridyl | H | 6-methyl-4-methoxypyridinyl |
| Ic-54 | 2-pyridyl | H | 5-methylpyridin-3-yl |
| Ic-55 | 2-pyridyl | H | 5-methyl-2-(thiophen-2-yl)pyridinyl |
| Ic-56 | 2-pyridyl | H | 5-methyl-6-methylpyridin-2-yl |
| Ic-57 | 2-pyridyl | H | 5-methyl-6-methoxypyridin-2-yl |
| Ic-58 | 2-pyridyl | H | 5-methyl-6-chloropyridin-2-yl |
| Ic-59 | 2-pyridyl | H | 5-methylpyridin-3-yl |

TABLE 6-continued

| | Ar¹ | Z¹ | Ar² |
|---|---|---|---|
| Ic-60 | 2-pyridyl | H | 2-chloro-4-methylpyridyl |
| Ic-61 | 2-pyridyl | H | 2-methoxy-4-methylpyridyl |
| Ic-62 | 2-pyridyl | H | 2-methyl-4-methylpyridyl |
| Ic-63 | 2-pyridyl | H | 5-methylpyrimidyl |
| Ic-64 | 2-pyridyl | H | 4-methylpyrimidyl |
| Ic-65 | 2-pyridyl | H | 4-methylpyrimidyl |
| Ic-66 | 2,6-dimethylpyridyl | H | 3-methylpyridyl |
| Ic-67 | 2-amino-6-methylpyridyl | H | 3-methylpyridyl |
| Ic-68 | quinoxalinyl | H | tolyl |
| Ic-69 | quinolinyl | H | tolyl |
| Ic-70 | isoquinolinyl | H | 3-methylpyridyl |
| Ic-71 | 2-pyridyl | Me | tolyl |
| Ic-72 | 2-pyridyl | Pen | tolyl |
| Ic-73 | 2-pyridyl | Br | tolyl |

TABLE 7

| | Ar¹ | n | Y¹ | Z¹ | Ar² |
|---|---|---|---|---|---|
| Ic-74 | 2-pyridyl | 1 | tolyl | H | tolyl |
| Ic-75 | 2-pyridyl | 1 | Me | H | tolyl |

TABLE 7-continued
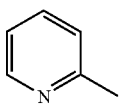
Ic
| | Ar¹ | n | Y¹ | Z¹ | Ar² |
|---|---|---|---|---|---|
| Ic-76 | 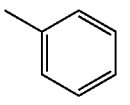<br>((COOH)₂) | 1 | Me | H | 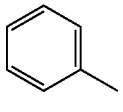 |
| Ic-77 | 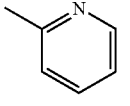 | 1 | CN | H | 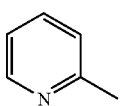 |
| Ic-78 | 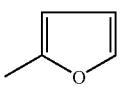 | 1 | H | H | 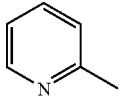 |
| Ic-79 | 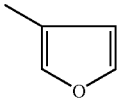 | 1 | H | H | 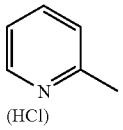 |
| Ic-80 | 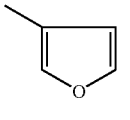<br>(HCl) | 1 | H | H | 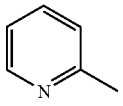 |
| Ic-81 | 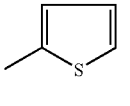 | 1 | H | H | 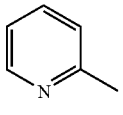 |
| Ic-82 | 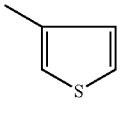 | 1 | H | H | 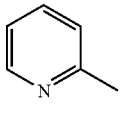 |
| Ic-83 | 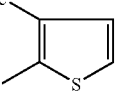 | 1 | H | H | 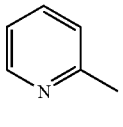 |
| Ic-84 | 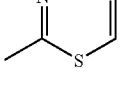 | 1 | H | H | 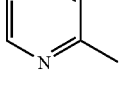 |
| Ic-85 | 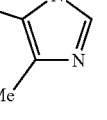 | 1 | H | H | 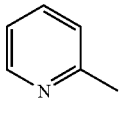 |
| Ic-86 | 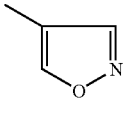 | 1 | H | H | |

TABLE 7-continued
Ic
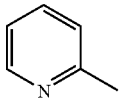
| | Ar¹ | n | Y¹ | Z¹ | Ar² |
|---|---|---|---|---|---|
| Ic-87 | 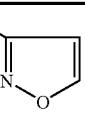 | 1 | H | H | 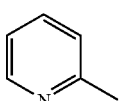 |
| Ic-88 |  | 1 | H | H | 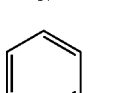 |
| Ic-89 |  | 1 | H | H | 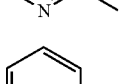 |
| Ic-90 |  | 1 | H | H | 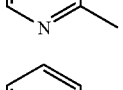 |
| Ic-91 |  | 1 | H | H | 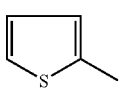 |
| Ic-92 |  | 1 | H | H | 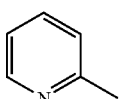 |
| Ic-93 |  | 2 | H | H | 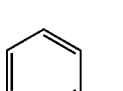 |
| Ic-94 |  | 2 | H | H | 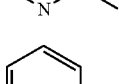 |
| Ic-95 |  | 2 | H | H | 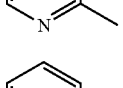 |
| Ic-96 |  | 2 | H | H | 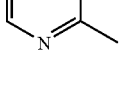 |
| Ic-97 |  | 2 | H | H | 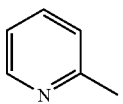 |
| Ic-98 |  | 2 | H | H | |

TABLE 7-continued

Ic

Ar¹—(═)ₙ═C(Z¹)—C(Y¹)—Ar²

| | Ar¹ | n | Y¹ | Z¹ | Ar² |
|---|---|---|---|---|---|
| Ic-99 | 2-methylpyridine | 2 | H | Me | 3-methylpyridine |
| Ic-100 | 2-methylpyridine | 2 | Me | H | 3-methylpyridine |
| Ic-101 | 2-methylpyridine | 2 | CN | H | 3-methylpyridine |
| Ic-102 | 2-methylpyridine | 2 | H | H | 4-methylpyridine |
| Ic-103 | 2-methylpyridine | 2 | H | H | 4-methylthiazole |
| Ic-104 | 2-methylpyridine | 2 | H | H | 3-methylthiophene |
| Ic-105 | 2-methylpyridine | 2 | H | H | 4-methylisoxazole |
| Ic-106 | 2-methylpyridine | 2 | H | H | 3-methylisoxazole |
| Ic-107 | 2-methylpyridine | 2 | H | H | 4-methyloxazole |
| Ic-108 | 2-methylpyridine | 2 | H | H | 3-methylpyrazole |
| Ic-109 | 2-methylpyridine (MeI) | 2 | H | H | 4-(NMe₂)phenyl |
| Ic-110 | 2-methylpyridine | 1 | H | CH₂O—* | 2-*-phenyl |

TABLE 7-continued

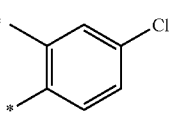

Ic

| | Ar¹ | n | Y¹ | Z¹ | Ar² |
|---|---|---|---|---|---|
| Ic-111 | 2-methylpyridine | 1 | Cl | CH₂S—* | 4-chlorophenyl (with * at 2-position) |

"CH₂O—*" and "CH₂S—*" each combine with * of Ar²

TABLE 8

Id

| | Ar¹ | X | Y¹ | Z¹ | Ar² |
|---|---|---|---|---|---|
| Id-1 | phenyl | CH₂ | H | H | 2-methylpyridine |
| Id-2 | phenyl | CH₂CH₂ | H | H | 2-methylpyridine |
| Id-3 | 2-methylpyridine | CH₂CH₂ | H | H | phenyl |
| Id-4 | 2-methylpyridine (HCl) | S | H | H | phenyl |
| Id-5 | 2-methylpyridine | NH | H | H | phenyl |
| Id-6 | 2-methylpyridine | N=CH | H | H | phenyl |

TABLE 9

*1) Solvent 1) CDCl3 + CD3OD 2) DMSO-d6 3) D2O 4) Oils in case of no value

| Compound | m.p (° C.) *4 | Molecular formula | Elemental anylysis (Calculated) | Elemental anylysis (Found) | NMR |
|---|---|---|---|---|---|
| Ia-1 | 76.5-78 | C14H10N2 | C, 81.53; H, 4.89; N, 13.58 | C, 81.48; H, 4.98; N, 13.27 | 7.49-7.63 (3H, m), 7.72-7.84 (2H, m), 8.10-8.24 (4H, m), 9.34 (1H, s) |
| Ia-2 | 138-139 | C14H9Cl1N2 | C, 69.86; H, 3.77; Cl, 14.73; N, 11.64 | C, 70.11; H, 3.65; Cl, 14.58; N, 11.78 | 7.54 (2H, d, J = 8.4), 7.72-7.85 (2H, m), 8.10-8.17 (2H, m), 8.16 (2H, d, J = 9.0), 9.30 (1H, s) |
| Ia-3 | 101-102 | C15H12N2O1 | C, 76.25; H, 5.12; N, 11.85 | C, 76.16; H, 5.08; N, 12.06 | 3.90 (3H, s), 7.08 (2H, d, J = 8.8), 7.66-7.82 (2H, m), 8.02-8.14 (2H, m), 8.18 (2H, d, J = 9.2), 9.29 (1H, s) |
| Ia-6 | 86-87 | C12H8N2S1 | C, 67.90; H, 3.80; N, 13.19; S, 15.10 | C, 67.82; H, 3.54; N, 13.29; S, 15.11 | 7.50 (1H, dd, J = 3.0, 5.2), 7.67-7.81 (2H, m), 7.92 (1H, dd, J = 1.6, 5.2), 8.06-8.12 (2H, m), 8.16 (1H, dd, J = 1.2, 3.0), 9.23 (1H, s) |
| Ia-10 | 126-127 | C20H14N2 | C, 85.08; H, 5.00; N, 9.92 | C, 85.33; H, 4.75; N, 9.87 | 7.38-7.52 (1H, m), 7.46-7.52 (2H, m), 7.67-7.70 (2H, m), 7.73-7.78 (2H, m), 7.81 (2H, d, J = 8.4), 8.12-8.19 (2H, m), 8.30 (2H, d, J = 8.4), 9.38 (1H, s) |
| Ia-12 | 180-182 | C21H15N1 | C, 89.65; H, 5.37; N, 4.98 | C, 89.87; H, 5.38; N, 5.06 | 7.35-7.40 (1H, m), 7.47 (2H, t, J = 7.8), 7.53 (1H, dt, J = 1.2, 7.5), 7.66-7.76 (3H, m), 7.76 (2H, d, J = 8.1), 7.83 (1H, d, J = 8.4), 7.93 (1H, d, J = 8.4), 8.18 (1H, d, J = 8.4), 8.23 (1H, d, J = 7.2), 8.26 (2H, d, J = 8.4) |

TABLE 9-continued

*1) Solvent 1) CDCl3 + CD3OD 2) DMSO-d6 3) D2O 4) Oils in case of no value

| Compound | m.p (°C.) *4 | Molecular formula | Elemental anylysis (Calculated) | Elemental anylysis (Found) | NMR |
|---|---|---|---|---|---|
| Ia-13 | on sale | | | | |
| Ia-14 | 120-123 | C16H13NO | C, 81.68; H, 5.57; N, 5.95 | C, 81.74; H, 5.50; N, 5.99 | 3.89 (3H, s), 7.05 (2H, d, J = 9.0), 7.45-7.86 (4H, m), 8.10-8.20 (2H, m), 8.14 (2H, d, J = 9.0) |
| Ia-15 | 132-133 | C13H9NS | C, 73.90; H, 4.29; N, 6.33; S, 15.18 | C, 73.96; H, 4.24; N, 6.61; S, 14.89 | 7.44 (1H, dd, J = 3.0 and 5.1), 7.47-7.53 (1H, m), 7.66-7.82 (3H, m), 7.88 (1H, dd, J = 1.2 and 5.1), 8.05 (1H, dd, J = 1.2 and 3.0), 8.08-8.20 (2H, m) |
| Ia-16 | 113-115 | C15H10ClN | C, 75.16, H, 4.20; N, 5.84; Cl, 14.79 | C, 75.09, H, 4.11; N, 5.73; Cl, 14.49 | 7.44-7.57 (1H, m), 7.50 (2H, d, J = 8.7), 7.69-7.88 (3H, m), 8.08-8.26 (2H, m), 8.13 (2H, d, J = 8.7) |

TABLE 10

| Compound | m.p (°C.) *4 | Molecular formula | Elemental anylysis (Calculated) | Elemental anylysis (Found) | NMR |
|---|---|---|---|---|---|
| Ia-17 | 153-156 | C22H17N1 | C, 89.46; H, 5.80; N, 4.74 | C, 89.43; H, 5.80; N, 4.79 | 2.79 (3H, s), 7.36-7.40 (1H, m), 7.47 (2H, t, J = 7.5), 7.55 (1H, dt, J = 1.5, 7.6), 7.68 (2H, dd, J = 2.1, 7.5), 7.72-7.77 (2H, m), 7.75 (2H, d, J = 8.1), 8.01 (1H, dd, J = 1.5, 8.4), 8.19 (1H, dd, J = 0.6, 9.0), 8.24 (2H, d, J = 8.4) |
| Ia-18 | 49-50 | C15H11N | C, 87.77; H, 5.40; N, 6.82 | C, 87.75; H, 5.50; N, 6.96 | 7.39-7.95 (8H, m), 8.16 (1H, d, J = 8.4), 8.32 (1H, d, J = 2.2), 9.19 (1H, d, J = 2.6) |
| Ia-19 | 233-234 | C14H12N2O 0.1AcOEt | C, 74.21; H, 5.54; N, 12.02 | C, 74.20; H, 5.66; N, 11.73 | CDCl3) 3.85 (3H, br), 6.98 (2H, d, J = 8.8), 7.25 (2H, dd, J = 3.2 and 6.0), 7.62 (2H, dd, J = 3.2 and 6.0), 8.01 (2H, d, J = 8.8) |
| Ia-20 | on sale | | | | |
| Ia-21 | on sale | | | | |
| Ia-22 | 95-97 | C14H11NO2 | C, 74.65; H, 4.92; N, 6.22 | C, 74.43; H, 4.98; N, 6.31 | CDCl3) 3.90 (3H, s), 7.03 (2H, d, J = 8.8), 7.23-7.40 (2H, m), 7.43-7.62 (1H, m), 7.68-7.79 (1H, m), 8.20 (2H, d, J = 8.8) |
| Ib-1 | 89-91 | C13H11N | C, 86.15; H, 6.12; N, 7.73 | C, 86.14; H, 6.09; N, 7.80 | 7.13-7.17 (1H, m), 7.17 (1H, d, J = 16.2), 7.30-7.41 (4H, m), 7.57-7.69 (4H, m), 8.60-8.62 (1H, m) |
| Ib-8 | on sale | | | | |
| Ib-9 | 122-124 | C14H10NF3 | C, 67.45; H, 4.04; N, 5.62; F, 22.87 | C, 67.31; H, 4.06; N, 5.67; S, 22.71 | 7.17-7.20 (1H, m), 7.24 (1H, d, J = 15.3), 7.40 (1H, d, J = 8.1), 7.61-7.73 (6H, m), 8.62-8.64 (1H, m) |
| Ib-10 | on sale | | | | |
| Ib-11 | on sale | | | | |
| Ib-15 | on sale | | | | |
| Ib-17 | 128 | C17H13N1 | C, 88.28; H, 5.67; N, 6.06 | C, 88.17; H, 5.73; N, 6.04 | 7.13-7.19 (1H, m), 7.33-7.50 (3H, m), 7.45 (1H, d, J = 16.4), 7.68 (1H, dt, J = 1.8, 7.7), 7.76-7.87 (5H, m), 7.90 (1H, d, J = 16.2), 8.63 (1H, d, J = 4.6) |
| Ib-18 | on sale | | | | |
| Ib-33 | 82-83 | C15H11N1O1 | C, 81.43; H, 5.01; N, 6.33 | C, 81.18; H, 5.03; N, 6.53 | 6.79 (1H, s), 7.13-7.33 (4H, m), 7.32 (1H, d, J = 15.8), 7.46-7.58 (2H, m), 7.62 (1H, d, J = 15.8), 7.67 (1H, dt, J = 1.8, 7.6), 8.61 (1H, d, J = 4.4) |

TABLE 11

| Compound | m.p (°C.) *4 | Molecular formula | Elemental anylysis (Calculated) | Elemental anylysis (Found) | NMR |
|---|---|---|---|---|---|
| Ib-34 | 122-124 | C14H10N2S1 | C, 70.56; H, 4.23; N, 11.75; S, 13.45 | C, 70.67; H, 4.30; N, 11.75; S, 13.44 | 7.12-7.28 (1H, m), 7.35-7.53 (3H, m), 7.62 (1H, d, J = 16.2), 7.72 (1H, dt, J = 1.8, 7.7), 7.84-7.90 (1H, m), 7.88 (1H, d, J = 15.8), 8.04 (1H, d, J = 7.6), 8.66 (1H, d, J = 4.4) |
| Ib-35 | 73-74 | C15H11N1O1 | C, 81.43; H, 5.01; N, 6.33 | C, 81.51; H, 5.10; N, 6.47 | 7.12-7.19 (1H, m), 7.28 (1H, d, J = 16.2), 7.34-7.40 (2H, m), 7.50-7.55 (1H, m), 7.67 (1H, dt, J = 1.6, 7.7), 7.45 (1H, d, J = 16.2), 7.85 (1H, s), 7.99 (1H, m), 8.61 (1H, d, J = 4.4) |
| Ib-36 | 73-75 | C16H14N2 | C, 82.02; H, 6.02; N, 11.96 | C, 82.00; H, 5.87; N, 11.95 | 3.80 (3H, s), 7.03-7.10 (1H, m), 7.15 (1H, d, J = 16.2), 7.19-7.36 (4H, m), 7.62 (1H, dt, J = 1.8, 7.6), 7.84 (1H, d, J = 16.6), 8.04 (1H, dd, J = 1.8, 6.6), 8.57 (1H, d, J = 4.8) |
| Ib-41 | 121.5-122 | C12H10N2 | C, 79.10; H, 5.53; N, 15.37 | C, 79.23; H, 5.49; N, 15.32 | 7.16-7.26 (2H, m), 7.41-7.45 (2H, m), 7.66-7.71 (4H, m), 8.62-8.65 (2H, m) |
| Ib-42 | on sale | | | | |
| Ib-43 | oil | C12H10N2 | C, 78.79; H, 5.51; N, 15.31 | C, 78.42; H, 5.59; N, 15.27 | 7.17-7.33 (3H, m), 7.50 (1H, d, J = 8.1), 7.61-7.72 (2H, m), 7.87-7.91 (1H, m), 8.52-8.53 (1H, m), 8.62-8.63 (1H, m), 8.80 (1H, s) |
| Ib-44 | on sale | | | | |
| Ib-45 | 70-73 | C12H10N2 0.1H2O | C, 78.32; H, 5.58; N, 15.22 | C, 78.22; H, 5.67; N, 15.10 | 7.20-7.24 (1H, m), 7.34 (1H, d, J = 16.2), 7.41-7.44 (3H, m), 7.58 (1H, d, J = 16.2), 7.68-7.74 (1H, m), 8.61-8.66 (3H, m) |
| Ib-46 | 103.5-105 | C11H9NS | C, 70.55; H, 4.84; N, 7.48; S, 17.12 | C, 70.55; H, 4.84; N, 7.45, S, 17.16 | 6.89 (1H, d, J = 16.2), 7.18 (1H, d, J = 16.2), 7.27-7.37 (4H, m), 7.78-7.82 (1H, m), 8.48 1H, br), 8.70 (1H, br) |
| Ib-47 | 180-182 | C11H9NS | C, 70.55; H, 4.84; N, 7.48; S, 17.12 | C, 70.37; H, 4.83; N, 7.59, S, 17.19 | 6.85 (1H, d, J = 16.2), 7.26-7.38 (6H, m), 8.57 (2H, br) |

TABLE 11-continued

| | | | | | |
|---|---|---|---|---|---|
| Ib-48 | 113.5-114.5 | C10H8N2S | C, 63.80; H, 4.28; N, 14.88; S, 17.03 | C, 63.95; H, 4.26; N, 14.55; S, 16.90 | 6.89 (1H, d, J = 15.9), 7.25-7.29 (1H, m), 7.35-7.41 (2H, m), 7.49-7.51 (1H, m), 7.90 (1H, d, J = 15.9), 8.66 (1H, br), 9.15 (1H, s) |
| Ib-49 | 74-76 | C10H8N2S•0.1H2O | C, 63.20; H, 4.24; N, 14.74; S, 16.87 | C, 63.31; H, 4.27; N, 14.57; S, 16.99 | 6.99 (1H, d, J = 15.9), 7.26-7.44 (3H, m), 7.75 (1H, d, J = 15.9), 8.39 (1H, br), 8.53 (1H, br), 8.61 (1H, br) |

TABLE 12

| | | | | | |
|---|---|---|---|---|---|
| Ib-50 | 95-96 | C12H12N2 | C, 78.23; H, 6.56; N, 15.20 | C, 78.37; H, 6.59; N, 15.28 | 3.75 (3H, s), 6.16-6.18 (1H, m), 6.59-6.61 (1H, m), 6.67-6.68 (1H, m), 6.90 (1H, d, J = 15.3), 7.05-7.10 (1H, m), 7.23-7.26 (1H, m), 7.56-7.63 (2H, m), 8.55-8.57 (1H, m) |
| Ib-51 | oil | C13H14N2O 0.1H2O | C, 72.27; H, 6.53; N, 12.96 | C, 72.22; H, 6.52; N, 12.96 | 3.28 (3H, s), 5.33 (2H, s), 6.21-6.23 (1H, m), 6.64-6.65 (1H, m), 6.82-6.83 (1H, m), 6.97 (1H, d, J = 16.2), 7.05-7.10 (1H, m), 7.28-7.31 (1H, m), 7.58-7.63 (1H, m), 7.63 (1H, d, J = 16.2), 8.55-8.57 (1H, m) |
| Ib-52 | 97-98.5 | C11H9NS | C, 70.55; H, 4.84; N, 7.48; S, 17.12 | C, 70.54; H, 4.75; N 7.65; S, 17.34 | 7.01 (1H, d, J = 16.0), 7.10-7.16 (1H, m), 7.31-7.40 (4H, m), 7.60-7.68 (2H, m), 8.58-8.59 (1H, m) |
| Ib-53 | 84-85 | C11H9N1O1 | C, 77.17; H, 5.30; N, 8.18 | C, 76.90; H, 5.40; N, 8.07 | 6.68 (1H, m), 6.88 (1H, d, J = 16.2), 7.08-7.15 (1H, m), 7.31 (1H, d, J = 8.2), 7.42 (1H, m), 7.50 (1H, d, J = 16.2), 7.59 (1H, s), 7.64 (1H, dt, J = 1.8, 7.7), 8.56 (1H, d, J = 4.6) |
| Ib-54 | 232-233 | C11H11N3 | C, 71.33; H, 5.99; N, 22.68 | C, 71.18; H, 5.99; N, 22.43 | *2) 2.28 (3H, s), 6.85-7.19 (2H, m), 7.45 (1H, d, J = 7.6), 7.52 (1H, d, J = 15.8), 7.70 (1H, dt, J = 1.6, 8.1), 8.50 (1H, d, J = 3.6) |
| Ib-55 | 61-63 | C12H12N3Cl | C, 61.67; H, 5.18; N, 17.98; Cl, 15.17 | C, 61.68; H, 5.32; N, 18.21; Cl, 15.12 | 2.43 (3H, s), 3.81 (3H, s), 7.04 (1H, d, J = 16.5), 7.10-7.14 (1H, m), 7.34 (1H, d, J = 7.8), 7.44 (1H, d, J = 16.5), 7.61-7.67 (1H, m), 8.58-8.60 (1H, m) |
| Ib-56 | 107-108 | C16H12N2 | C, 82.73; H, 5.21; N, 12.06 | C, 82.57; H, 5.07; N, 11.99 | 7.39 (1H, d, J = 16.6), 7.36-7.48 (3H, m), 7.65-7.81 (4H, m), 7.88 (1H, d, J = 16.6), 8.08 (1H, dd, J = 2.4, 6.8), 9.05 (1H, s) |
| Ib-57 | 117-119 | C17H14N2 | C, 82.90; H, 5.73; N, 11.37 | C, 83.12; H, 5.73; N, 11.17 | 2.40 (3H, s), 7.24 (2H, d, J = 8.4), 7.34 (1H, d, J = 16.0), 7.56 (2H, d, J = 8.4), 7.65-7.81 (2H, m), 7.85 (1H, d, J = 16.0), 8.06 (2H, m), 9.04 (1H, s) |
| Ib-58 | 162-163 | C18H14N2O2 | C, 74.47; H, 4.86; N, 9.65 | C, 74.41; H, 4.85; N, 9.55 | 3.94 (3H, s), 7.47 (1H, d, J = 16.2), 7.72 (2H, d, J = 8.4), 7.72-7.81 (2H, m), 7.91 (1H, d, J = 16.6), 8.08 (2H, m), 8.09 (2H, d, J = 8.4), 9.05 (1H, s) |
| Ib-59 | >300 | C17H12N2O2 | C, 73.90; H, 4.38: N, 10.14 | C, 73.81; H, 4.39; N, 10.21 | *2) 3.38 (1H, br.s), 7.72 (1H, d, J = 16.6), 7.78-7.85 (2H, m), 7.90 (2H, d, J = 8.0), 8.01 (2H, d, J = 8.8), 8.07 (1H, d, J = 15.8), 8.09 (2H, m), 9.30 (1H, s) |

TABLE 13

| | | | | | |
|---|---|---|---|---|---|
| Ib-60 | 206-208 | C17H11N3 | C, 79.36; H, 4.31; N, 16.33 | C, 79.47; H, 4.37; N, 16.26 | 7.47 (1H, d, J = 16.0), 7.70 (2H, d, J = 8.8), 7.75 (2H, d, J = 8.8), 7.74-7.83 (2H, m), 7.89 (1H, d, J = 16.6), 8.07-8.12 (2H, m), 9.04 (1H, s) |
| Ib-61 | 131-133 | C22H16N2 | C, 85.68; H, 5.23; N, 9.08 | C, 85.97; H, 5.13; N, 9.23 | 7.37-7.51 (3H, m), 7.43 (1H, d, J = 16.4), 7.62-7.82 (4H, m), 7.66 (2H, d, J = 8.8), 7.75 (2H, d, J = 8.4), 7.92 (1H, d, J = 16.6), 8.08 (1H, dd, J = 2.6, 7.8), 9.06 (1H, s) |
| Ib-64 | 124-126 | C16H11F1N2 | C, 76.79; H, 4.43; F, 7.59; N, 11.19 | C, 76.89; H, 4.43; F, 7.35; N, 11.23 | 7.12 (2H, t, J = 8.6), 7.30 (1H, d, J = 16.0), 7.60-7.77 (4H, m), 7.84 (1H, d, J = 16.4), 8.04-8.10 (2H, m), 9.02 (1H, s) |
| Ib-65 | 144-145 | C16H11Cl1N2 | C, 72.05; H, 4.16; Cl, 13.29; N, 10.50 | C, 72.05; H, 4.05; Cl, 13.09; N, 10.47 | 7.35 (1H, d, J = 16.2), 7.39 (2H, d, J = 8.4), 7.59 (2H, d, J = 8.4), 7.67-7.82 (2H, m), 7.83 (1H, d, J = 16.6), 8.04-8.10 (2H, m), 9.02 (1H, s) |
| Ib-66 | 164-165 | C16H11Br1N2 | C, 61.76; H, 3.56; Br, 25.68; N, 9.00 | C, 61.58; H, 3.58; Br, 25.52; N, 8.98 | 7.36 (1H, d, J = 16.0), 7.51 (2H, d, J = 8.4), 7.56 (2H, d, J = 8.4), 7.67-7.82 (2H, m), 7.82 (1H, d, J = 16.2), 8.04-8.10 (2H, m), 9.02 (1H, s) |
| Ib-67 | 130-131 | C17H14N2O1 | C, 77.84; H, 5.38; N, 10.68 | C, 78.13; H, 5.36; N, 10.70 | 6.95 (2H, d, J = 8.8), 7.25 (1H, d, J = 16.6), 7.61 (2H, d, J = 8.8), 7.65-7.78 (2H, m), 7.83 (1H, d, J = 16.4), 8.05 (2H, td, J = 2.0, 7.4), 9.02 (1H, s) |
| Ib-68 | 234-235 | C1612N2O1 | C, 77.40; H, 4.87; N, 11.28 | C, 77.36; H, 4.81; N, 11.39 | *1) 6.89 (2H, d, J = 8.8), 7.21 (1H, d, J = 16.4), 7.55 (2H, d, J = 8.8), 7.65-7.81 (2H, m), 7.80 (1H, d, J = 16.0), 8.04 (2H, dd, J = 2.2, 7.6), 9.03 (1H, s) |
| Ib-69 | 166-167 | C16H13N3 0.1H2O | C, 77.15; H, 5.34; N, 16.87 | C, 77.12; H, 5.03; N, 16.98 | 1.2-4.4 (2H, br.), 6.71 (2H, d, J = 8.4), 7.19 (1H, d, J = 16.4), 7.49 (2H, d, J = 8.6), 7.62-7.77 (2H, m), 7.79 (1H, d, J = 16.0), 8.01-8.06 (2H, m), 9.00 (1H, s) |
| Ib-70 | 225-227 | C18H15N3O1 0.3H2O | C, 73.35; H, 5.33; N, 14.26 | C, 73.37; H, 5.31; N, 14.21 | *1) 2.19 (3H, s), 7.31 (1H, d, J = 16.6), 7.61 (4H, s), 7.67-7.82 (2H, m), 7.82 (1H, d, J = 16.4), 8.06 (2H, dd, J = 2.2, 7.4), 9.03 (1H, s) |
| Ib-72 | 121-122 | C22H16N2O1 | C, 81.46; H, 4.97; N, 8.63 | C, 81.83; H, 4.91; N, 8.50 | 7.04 (2H, d, J = 8.8), 7.09-7.42 (5H, m), 7.29 (1H, d, J = 16.2), 7.63 (2H, d, J = 8.8), 7.69-7.79 (2H, m), 7.85 (1H, d, J = 16.0), 8.08 (2H, td, J = 2.2, 7.2), 9.03 (1H, s) |

TABLE 14

| | | | | | |
|---|---|---|---|---|---|
| Ib-73 | 98-101 | C14H10N2O1 | C, 75.66; H, 4.54; N, 12.60 | C, 75.56; H, 4.56; N, 12.75 | 6.50 (1H, dd, J = 1.5, 3.3), 6.61 (1H, d, J = 3.0), 7.29 (1H, d, J = 15.9), 7.51 (1H, d, J = 1.5), 7.66-7.78 (2H, m), 7.72 (1H, d, J = 16.2), 8.03-8.07 (2H, m), 8.93 (1H, s) |
| Ib-74 | 97-99 | C14H10N2S1 | C, 70.56; H, 4.23; N, 11.75; S, 13.45 | C, 70.39; H, 4.13; N, 11.96; S, 13.44 | 7.08 (1H, dd, J = 3.6, 5.2), 7.17 (1H, d, J = 16.2), 7.30 (1H, d, J = 3.4), 7.35 (1H, d, J = 5.0), 7.65-7.80 (2H, m), 7.98-8.08 (2H, m), 8.03 (1H, d, J = 16.2), 8.96 (1H, s) |
| Ib-75 | 107-109 | C14H10N2O1 | C, 75.66; H, 4.54; N, 12.60 | C, 75.78; H, 4.51; N, 12.56 | 6.77 (1H, m), 7.12 (1H, d, J = 16.2), 7.48 (1H, m), 7.67-7.79 (3H, m), 7.77 (1H, d, J = 16.2), 8.03-8.08 (2H, m), 8.99 (1H, s) |
| Ib-77 | 97-99 | C14H10N2S1 | C, 70.56; H, 4.23; N, 11.75; S, 13.35 | C, 70.39; H, 4.25; N, 11.86; S, 13.24 | 7.21 (1H, d, J = 16.0), 7.39 (1H, dd, J = 3.0, 5.2), 7.47 (1H, dd, J = 1.0, 5.2), 7.52 (1H, dd, J = 2.8, 1.0), 7.65-7.80 (2H, m), 7.88 (1H, d, J = 16.4), 8.02-8.09 (2H, m), 9.01 (1H, s) |
| Ib-84 | 129-131 | C14H10N2O1 | C, 75.66; H, 4.53; N, 12.60 | C, 75.44; H, 4.44; N, 12.50 | 7.23-7.30 (1H, m), 7.33-7.57 (4H, m), 7.62 (1H, d, J = 15.8), 7.69-7.78 (2H, m), 7.82 (1H, d, J = 15.6), 8.68 (1H, d, J = 4.4) |
| Ib-85 | on sale | | | | |
| Ib-87 | 128-129.5 | C13H9NS2 | C, 64.17; H, 3.73; N, 5.76; S, 26.35 | C, 64.17; H, 3.71; N, 5.86; S, 26.18 | 7.24 (1H, d, J = 16.2), 7.34-7.39 (3H, m), 7.44-7.50 (2H, m), 7.54 (1H, d, J = 16.2), 7.87 (1H, d, J = 8.1), 7.98 (1H, d, J = 8.1) |
| Ib-88 | 59-60 | C23H23NO3 | C, 76.43; H, 6.41; N, 3.88 | C, 76.63; H, 6.39; N, 4.07 | 1.27 (3H, t, J = 7.2), 2.10-2.19 (2H, m), 2.54 (2H, t, J = 7.2), 4.07 (2H, t, J = 6.2), 4.17 (2H, q, J = 7.2), 6.87 (1H, dd, J = 2.4 and 8.1), 7.18-7.52 (5H, m), 7.62-7.80 (4H, m), 8.07-8.15 (2H, m) |
| Ib-89 | 157-159 | C21H19NO3 | C, 75.66; H, 5.74; N, 4.20 | C, 75.72; H, 5.68; N, 4.23 | 2.15-2.24 (2H, m), 2.66 (2H, t, J = 7.2), 4.14 (2H, t, J = 6.2), 6.86-6.90 (1H, m), 7.14-7.17 (1H, m), 7.29-7.31 (2H, m), 7.48-7.60 (3H, m), 7.68-7.80 (3H, m), 8.12-8.16 (2H, m) |
| Ib-91 | 134-135 | C15H11NS | C, 75.92; H, 4.67; N, 5.90; S, 13.51 | C, 76.00; H, 4.84; N, 5.91; S, 13.47 | 7.25 (1H, d, J = 16.2), 7.34-7.37 (1H, m), 7.44-7.52 (3H, m), 7.62-7.80 (4H, m), 8.05-8.13 (2H, m) |
| Ib-100 | 101-102 | C11H9NS | C, 70.55; H, 4.84; N, 7.48; S, 17.12 | C, 70.64; H, 4.84; N, 7.52; S, 17.16 | 6.97 (1H, d, J = 15.7), 7.01-7.04 (1H, m), 7.11-7.18 (2H, m), 7.24-7.32 (2H, m), 7.61-7.67 (1H, m), 7.79 (1H, d, J = 15.7), 8.58-8.59 (1H, m) |

TABLE 15

| | | | | | |
|---|---|---|---|---|---|
| Ib-101 | on sale | | | | |
| Ib-102 | 170-172 | C15H11N3O | C, 72.28; H, 4.45; N, 16.86 | C, 72.27; H, 4.48; N, 16.95 | 7.19 (1H, d, J = 16.8), 7.39 (1H, dd, J = 4.8 and 8.1), 7.50-7.60 (3H, m), 7.64 (1H, d, J = 16.8), 7.89-7.96 (1H, m), 8.09-8.19 (2H, m), 8.63 (1H, d, J = 4.2), 8.82 (1H, s) |
| Ib-103 | 142-143 | C16H13N3O2 | C, 68.81; H, 4.69; N, 15.04 | C, 68.93; H, 4.52; N, 14.97 | 3.91 (3H, s), 7.08-7.14 (1H, m), 7.18 (1H, d, J = 16.2), 7.38 (1H, dd, J = 4.8 and 8.1), 7.45 (1H, t, J = 8.1), 7.63 (1H, d, J = 16.2), 7.64-7.74 (2H, m), 7.88-7.96 (1H, m), 8.63 (1H, dd, J = 1.5 and 4.8), 8.81 (1H, d, J = 2.1) |
| Ic-1 | 122-124 | C15H13N1 | C, 86.92; H, 6.32; N, 6.76 | C, 86.94; H, 6.34; N, 6.83 | 6.72 (1H, d, J = 15.4), 6.78 (1H, d, J = 15.4), 6.96 (1H, d, J = 10.0), 7.06-7.14 (1H, m), 7.24-7.50 (7H, m), 7.62 (1H, dt, J = 1.8, 7.7), 8.57 (1H, d, J = 4.6) |
| Ic-2 | | C16H15N1 | | | 2.38 (3H, s), 6.72 (1H, d, J = 15.4), 6.93 (1H, d, J = 15.4), 6.92-7.32 (6H, m), 7.46 (1H, d, J = 15.0), 7.51 (1H, d, J = 15.4), 7.63 (1H, dt, J = 1.8, 7.6), 8.58 (1H, d, J = 4.8) |
| Ic-4 | 63-64 | C16H15N1 | C, 86.84; H, 6.83; N, 6.33 | C, 86.98; H, 6.74; N, 6.48 | 2.36 (3H, s), 6.72 (1H, d, J = 15.2), 6.75 (1H, d, J = 15.4), 6.96 (1H, d, J = 15.4), 7.05-7.14 (2H, m), 7.19-7.49 (5H, m), 7.62 (1H, dt, J = 1.8, 7.7), 8.57 (1H, d, J = 4.8) |
| Ic-6 | 126-127 | C16H15N1 | C, 86.84; H, 6.83; N, 6.33 | C, 86.75; H, 6.89; N, 6.23 | 2.35 (3H, s), 6.69 (1H, d, J = 15.0), 6.75 (1H, d, J = 15.4), 6.96 (1H, dd, J = 15.4, 10.6), 7.06-7.10 (1H, m), 7.14 (2H, d, J = 8.0), 7.27-7.49 (2H, m), 7.36 (2H, d, J = 8.4), 7.62 (1H, dt, J = 1.8, 7.7), 8.56 (1H, d, J = 4.2) |
| Ic-9 | 125-127 | C16H12F3N1 | C, 69.81; H, 4.39; F, 20.70; N, 5.09 | C, 69.85; H, 4.26; F, 20.70; N, 5.12 | 6.79 (1H, d, J = 15.2), 7.07 (1H, dd, J = 10.6, 15.4), 7.10-7.17 (1H, m), 7.29-7.52 (2H, m), 7.54 (2H, d, J = 8.8), 7.59 (2H, d, J = 8.8), 7.65 (1H, dt, J = 1.8, 7.7), 8.59 (1H, d, J = 4.8) |
| Ic-11 | 108-109 | C16H15N1O1 | C, 80.98; H, 6.37; N, 5.90 | C, 80.87; H, 6.45; N, 6.07 | 3.82 (3H, s), 6.67 (1H, d, J = 15.4), 6.73 (1H, d, J = 15.4), 6.81-6.94 (1H, m), 6.87 (2H, d, J = 8.4), 7.05-7.12 (1H, m), 7.27-7.48 (2H, m), 7.40 (2H, d, J = 8.8), 7.61 (1H, dt, J = 1.8, 7.7), 8.56 (1H, d, J = 4.8) |

TABLE 16

| | | | | | |
|---|---|---|---|---|---|
| Ic-15 | 110-111 | C17H17N1O1 | C, 81.24; H, 6.82; N, 5.57 | C, 81.40; H, 6.74; N, 5.57 | 2.23 (3H, s), 3.84 (3H, s), 6.66 (1H, d, J = 15.4), 6.71 (1H, d, J = 15.4), 6.79 (1H, d, J = 7.6), 6.87 (1H, dd, J = 10.2, 15.4), 7.05-7.11 (1H, m), 7.23-7.31 (3H, m), 7.41 (1H, dd, J = 9.8, 15.4), 7.61 (1H, dt, J = 1.8, 7.6), 8.56 (1H, d, J = 4.8) |
| Ic-18 | 116-117 | C18H17N1O3 | C, 73.20; H, 5.80; N, 4.74 | C, 73.01; H, 5.72; N, 4.84 | 2.31 (3H, s), 3.88 (3H, s), 6.73 (2H, d, J = 15.8), 6.88-7.02 (3H, m), 7.03 (1H, d, J = 1.2), 7.08-7.15 (1H, m), 7.30 (1H, d, J = 8.0), 7.43 (1H, dd, J = 10.2, 15.0), 7.63 (1H, dt, J = 1.8, 7.6), 8.57 (1H, d, J = 4.4) |
| Ic-19 | 147-148 | C16H15N1O2 | C, 75.87; H, 5.97; N, 5.53 | C, 75.77; H, 6.05; N, 5.58 | 3.94 (3H, s), 5.83 (1H, br.s), 6.68 (1H, d, J = 15.4), 6.70 (1H, d, J = 15.4), 6.85 (1H, dd, J = 10.0, 15.4), 6.86-7.01 (2H, m), |

TABLE 16-continued

| | | | | | |
|---|---|---|---|---|---|
| | | | | | 6.97 (1H, d, J = 1.2), 7.06-7.12 (1H, m), 7.29 (1H, d, J = 8.0), 7.41 (1H, dd, J = 10.2, 15.4), 7.62 (1H, dt, J = 1.8, 7.6), 8.56 (1H, d, J = 4.4) |
| Ic-39 | 111-112 | C15H12N2O2 | C, 71.42; H, 4.79; N, 11.10 | C, 71.42; H, 4.79; N, 11.07 | 6.81 (1H, d, J = 15.4), 6.95 (1H, d, J = 15.4), 7.01 (1H, d, J = 15.4), 7.11-7.18 (1H, m), 7.25-7.75 (6H, m), 7.93 (1H, dd, J = 1.2, 8.0), 8.59 (1H, d, J = 4.8) |
| Ic-40 | 174-175 | C15H12N2O2 | C, 71.42; H, 4.79; N, 11.10 | C, 71.45; H, 4.64; N, 11.09 | 6.81 (2H, d, J = 15.4), 6.84 (1H, d, J = 15.4), 7.12 (1H, d, J = 15.4), 7.17-7.26 (1H, m), 7.31-7.49 (2H, m), 7.58 (2H, d, J = 8.8), 7.67 (1H, dt, J = 1.8, 7.6), 8.21 (2H, d, J = 8.8), 8.61 (1H, d, J = 4.8) |
| Ic-41 | 122-123 | C15H12F1N1 | C, 79.98; H, 5.37; F, 8.43; N, 6.22 | C, 80.07; H, 5.31; F, 8.43; N, 6.21 | 6.71 (1H, d, J = 15.4), 6.93 (1H, d, J = 15.8), 6.85-6.93 (1H, m), 7.01 (2H, d, J = 8.8), 7.08-7.14 (1H, m), 7.28-7.48 (2H, m), 7.41 (2H, d, J = 8.2), 7.63 (1H, dt, J = 1.8, 7.8), 8.57 (1H, d, J = 4.4) |

TABLE 17

| | | | | | |
|---|---|---|---|---|---|
| Ic-44 | 124-126 | C16H15N1S1 | C, 75.85; H, 5.97; N, 5.53; S, 12.66 | C, 75.82; H, 5.82; N, 5.67; S, 12.66 | 2.49 (3H, s), 6.71 (1H, d, J = 15.4), 6.73 (1H, d, J = 15.4), 6.96 (1H, dd, J = 10.6, 15.4), 7.07-7.14 (1H, m), 7.21 (2H, d, J = 8.4), 7.26-7.49 (2H, m), 7.38 (2H, d, J = 8.4), 7.62 (1H, dt, J = 1.8, 7.7), 8.56 (1H, d, J = 4.4) |
| Ic-45 | 195-199 | C17H16N2O1 | C, 77.25; H, 6.10; N, 10.60 | C, 77.09; H, 5.99; N, 10.78 | 2.18 (3H, s), 6.70 (1H, d, J = 15.4), 6.73 (1H, d, J = 15.4), 6.87-7.00 (1H, m), 7.06 (1H, m), 7.25-7.55 (2H, m), 7.41 (2H, d, J = 9.2), 7.49 (2H, d, J = 9.2), 7.62 (1H, dt, J = 1.8, 7.7), 8.57 (1H, d, J = 4.4) |
| Ic-46 | 165-167 | C17H18N2 | C, 81.56; H, 7.25; N, 11.19 | C, 81.58; H, 7.19; N, 11.12 | 2.98 (6H, s), 6.62 (2H, d, J = 15.0), 6.70-6.89 (3H, m), 7.02-7.09 (1H, m), 7.29-7.47 (2H, m), 7.36 (2H, d, J = 8.8), 7.59 (1H, dd, 1.8, 7.9), 8.54 (1H, d, J = 4.2) |
| Ic-47 | on sale | | | | |
| Ic-48 | 119-121 | C14H12N2 | C, 80.74; H, 5.81; N, 13.45 | C, 80.98; H, 5.78; N, 13.29 | 6.83 (1H, d, J = 11.6), 6.84 (1H, d, J = 11.4), 7.10-7.16 (2H, m), 7.31-7.41 (2H, m), 7.48 (2H, dd, J = 3.0, 11.4), 7.64 (2H, dt, J = 1.8, 7.7), 8.59 (2H, d, J = 4.8) |
| Ic-54 | 87-88 | C14H12N2 | C, 80.74; H, 5.81; N, 13.45 | C, 80.78; H, 5.74; N, 13.58 | 6.75 (1H, d, J = 10.4), 6.77 (1H, d, J = 10.2), 7.00-7.16 (2H, m), 7.24-7.33 (2H, m), 7.45 (1H, dd, J = 7.0, 10.4), 7.64 (1H, dt, J = 1.0, 5.1), 7.77 (1H, td, J = 1.2, 5.4), 8.48 (1H, d, J = 3.0), 8.59 (1H, td, J = 1.2, 3.2), 8.59 (1H, s) |
| Ic-59 | 112-114 | C14H12N2 | C, 80.74; H, 5.81; N, 13.45 | C, 80.82; H, 5.80; N, 13.26 | 6.69 (1H, d, J = 15.4), 6.82 (1H, d, J = 15.4), 7.10-7.18 (2H, m), 7.23-7.34 (1H, m), 7.30 (2H, d, J = 6.2), 7.46 (1H, dd, J = 11.0, 15.4), 7.65 (1H, dt, J = 1.8, 7.7), 8.56 (2H, d, J = 6.2), 8.60 (1H, d, J = 4.8) |
| Ic-68 | 118-120 | C18H14N2 | C, 83.69; H, 5.46; N, 10.84 | C, 84.14; H, 5.35; N, 10.92 | 6.95 (2H, d, J = 15.0), 7.08 (1H, dd, J = 9.9, 15.6), 7.29-7.40 (3H, m), 7.51 (2H, dd, J = 1.8, 8.7), 7.65-7.77 (3H, m), 8.02-8.06 (2H, m), 8.95 (1H, s) |
| Ic-71 | 61-62 | C16H15N1 | C, 86.84; H, 6.83; N, 6.33 | C, 86.79; H, 6.87; N, 6.51 | 2.15 (3H, d, J = 1.0), 6.73 (1H, d, J = 16.2), 6.79 (1H, s), 7.07-7.14 (1H, m), 7.25-7.37 (6H, m), 7.46 (1H, d, J = 15.8), 7.63 (1H, dt, J = 1.8, 7.7), 8.58 (1H, d, J = 4.6) |

TABLE 18

| | | | | | |
|---|---|---|---|---|---|
| Ic-72 | | C20H23N1 | | | 0.91 (3H, t, J = 7.0), ca.1.38 (4H), ca.1.60 (2H), 2.57 (2H, t, J = 8.1), 6.73 (1H, d, J = 15.8), 6.74 (1H, s), 7.07-7.14 (1H, m), 7.28-7.39 (7H, m), 7.63 (1H, dt, J = 1.8, 7.7), 8.57 (1H, d, J = 4.2) |
| Ic-73 | 113-114 | C15H12Br1N1 | C, 62.96; H, 4.23; Br, 27.92; N, 4.89 | C, 62.97; H, 4.27; Br, 27.63; N, 5.11 | 7.09 (1H, d, J = 14.2), 7.15-7.21 (1H, m), 7.22 (1H, s), 7.30-7.45 (4H, m), 7.56 (1H, d, J = 14.8), 7.66 (1H, dt, J = 1.8, 7.7), 7.73-7.78 (2H, m), 8.59 (1H, d, J = 4.2) |
| Ic-74 | | C21H17N1 | | | 6.82 (1H, d, J = 15.4), 6.93 (1H, d, J = 11.0), 7.02-7.08 (1H, m), 7.22-7.43 (12H, m), 7.56 (1H, dt, J = 1.8, 7.7), 8.49 (1H, d, J = 4.2) |
| Ic-75 | | C16H15N1 | | | 2.32 (3H, s), 6.67 (1H, s), 6.73 (1H, d, J = 5.4), 7.06-7.13 (1H, m), 7.27-7.40 (4H, m), 7.49-7.54 (2H, m), 7.62 (1H, dt, J = 1.8, 7.4), 7.72 (1H, dd, J = 11.8, 15.0), 8.58 (1H, d, J = 4.8) |
| Ic-76 | 124-126 | C16H15N1 (CO2H)2 | C, 69.44; H, 5.50; N, 4.50 | C, 69.61; H, 5.51; N, 4.46 | *3) 2.30 (3H, s), 6.68 (1H, d, J = 15.0), 6.80 (1H, d, J = 11.0), 7.30-7.42 (3H, m), 7.55-7.60 (2H, m), 7.65 (1H, t, J = 6.6), 7.83 (1H, dd, J = 11.0, 15.4), 8.05 (1H, d, J = 8.4), 8.31 (1H, dt, J = 1.8, 7.2), 8.38 (1H, d, J = 5.8) |
| Ic-77 | 94-95 | C16H12N2 | C, 82.73; H, 5.21; N, 12.06 | C, 82.71; H, 5.16; N, 12.18 | 7.15 (1H, d, J = 15.4), 7.21-7.28 (1H, m), 7.25 (1H, s), 7.36-7.49 (3H, m), 7.55-7.67 (3H, m), 7.76 (1H, dt, J = 1.8, 7.2), 8.22 (1H, d, J = 11.4), 8.61 (1H, d, J = 4.8) |
| Ic-78 | 86-88 | C13H11N1O1 | C, 79.17; H, 5.62; N, 7.10 | C, 79.20; H, 5.45; N, 7.11 | 6.35 (1H, d, J = 3.2), 6.42 (1H, dd, J = 1.8, 3.2), 6.56 (1H, d, J = 15.4), 6.70 (1H, d, J = 15.4), 6.90 (1H, dd, J = 11.0, 15.4), 7.06-7.13 (1H, m), 7.26-7.45 (2H, m), 7.39 (1H, d, J = 1.8), 7.61 (1H, dt, J = 1.8, 7.7), 8.56 (1H, d, J = 4.8) |
| Ic-79 | 96-98 | C13H11N1O1 | C, 79.17; H, 5.62; N, 7.10 | C, 79.38; H, 5.55; N, 7.20 | 6.65 (2H, d, J = 15.0), 6.66-6.70 (2H, m), 7.06-7.13 (1H, m), 7.26-7.44 (3H, m), 7.05 (1H, s), 7.61 (1H, dt, J = 1.8, 7.7), 8.56 (1H, d, J = 4.8) |

TABLE 18-continued

| | | | | | |
|---|---|---|---|---|---|
| Ic-80 | 180-181 | C13H11N1O1 HCl 0.25H2O | C, 65.55; H, 5.29; Cl, 14.37; N, 5.88 | C, 65.80; H, 5.56; Cl, 14.37; N, 5.71 | *3) 6.67 (2H, d, J = 12.2), 6.80 (1H, dd, J = 7.0, 10.4), 6.95 (1H, d, J = 10.2), 7.49-7.68 (4H, m), 8.08 (1H, d, J = 5.4), 8.36 (1H, t, J = 5.4), 8.43 (1H, d, J = 4.0) |

TABLE 19

| | | | | | |
|---|---|---|---|---|---|
| Ic-81 | 115-117 | C13H11N1S1 | C, 73.20; H, 5.20; N, 6.57; S, 15.03 | C, 73.37; H, 5.11; N, 6.62; S, 14.79 | 6.68 (1H, d, J = 15.4), 6.77-6.88 (2H, m), 6.96-7.05 (2H, m), 7.07-7.13 (1H, m), 7.19-7.29 (2H, m), 7.39 (1H, dd, J = 10.0, 15.0), 7.62 (1H, dt, J = 1.8, 7.7), 8.56 (1H, d, J = 4.4) |
| Ic-82 | 120-122 | C13H11N1O1 | C, 73.20; H, 5.20; N, 6.57; S, 15.03 | C, 73.50; H, 5.20; N, 6.46; S, 14.89 | 6.69 (1H, d, J = 15.4), 6.80 (1H, s), 6.82 (1H, d, J = 3.8), 7.07-7.13 (1H, m), 7.23-7.46 (5H, m), 7.62 (1H, dt, J = 1.8, 7.6), 8.57 (1H, d, J = 4.6) |
| Ic-83 | 71-73 | C14H13N1S1 | C, 73.97; H, 5.76; N, 6.16; S, 14.10 | C, 73.80; H, 5.75; N, 6.26; S, 14.13 | 2.27 (3H, s), 6.66 (1H, d, J = 15.4), 6.70 (1H, d, J = 15.2), 6.81 (1H, d, J = 5.2), 6.94 (1H, d, J = 15.0), 7.11 (1H, d, J = 5.2), 7.26 (1H, d, J = 4.8), 7.43 (1H, dd, J = 10.6, 15.2), 7.61 (1H, dt, J = 1.8, 7.6), 8.56 (1H, d, J = 4.8) |
| Ic-84 | 112-113 | C12H10N2S1 | C, 67.26; H, 4.70; N, 13.07; S, 14.96 | C, 67.47; H, 4.61; N, 13.02; S, 14.99 | 6.84 (1H, d, J = 15.0), 6.98 (1H, d, J = 15.0), 7.12-7.19 (1H, m), 7.21-7.39 (3H, m), 7.45 (1H, dd, J = 10.6, 14.6), 7.66 (1H, dt, J = 1.8, 7.7), 7.80 (1H, d, J = 3.4), 8.59 (1H, d, J = 4.8) |
| Ic-85 | 160-162 | C13H13N3 | C, 73.91; H, 6.20; N, 19.89 | C, 73.64; H, 6.07; N, 19.76 | 2.32 (3H, s), 6.61 (1H, d, J = 15.4), 6.67 (1H, d, J = 15.4), 6.81-6.94 (1H, m), 7.05-7.12 (1H, m), 7.26-7.30 (1H, m), 7.40 (1H, dd, J = 10.2, 15.0), 7.56 (1H, s), 7.61 (1H, dt, J = 1.8, 7.6), 8.54 (1H, d, J = 4.8) |
| Ic-93 | 154-155 | C15H13N1O1 | C, 80.69; H, 5.87; N, 6.27 | C, 80.65; H, 5.85; N, 6.29 | 6.49-6.63 (5H, m), 6.62 (1H, d, J = 15.8), 7.05-7.12 (1H, m), 7.26-7.33 (2H, m), 7.38 (1H, m), 7.47 (1H, s), 7.61 (1H, dt, J = 1.8, 7.6), 8.55 (1H, d, J = 4.2) |
| Ic-109 | on sale | | | | |
| Ic-110 | 114 | C16H13N1O1 | C, 81.68; H, 5.57; N, 5.95 | C, 81.74; H, 5.36; N, 5.91 | 5.10 (2H, s), 6.50 (1H, d, J = 16.2), 6.62 (1H, s), 6.80-6.92 (2H, m), 7.03-7.16 (3H, m), 7.31 (1H, d, J = 7.4), 7.37 (1H, d, J = 15.8), 7.64 (1H, dt, J = 1.8, 7.7), 8.58 (1H, d, J = 4.6) |
| Ic-111 | 137.5-139.5 | C16H11NSCl2 | C, 60.00; H, 3.46; N, 4.37; S, 10.01; Cl, 22.14 | C, 59.97; H, 3.51; N, 4.23; S, 10.07; Cl, 22.14, | 3.76 (2H, s), 6.92 (1H, d, J = 15.9), 7.13-7.26 (3H, m), 7.60 (1H, d, J = 8.1), 7.66-7.71 (1H, m), 7.79 (1H, d, J = 2.1), 8.05 (1H, d, J = 15.9), 8.63 (1H, d, J = 4.5) |

TABLE 20

| | | | | | |
|---|---|---|---|---|---|
| Id-1 | | C14H13N1 | | | 3.59 (2H, d, J = 6.6), 6.52 (1H, d, J = 15.8), 6.68 (1H, td, J = 6.8, 15.8), 7.05-7.11 (1H, m), 7.21-7.35 (6H, m), 7.59 (1H, dt, J = 1.8, 7.6), 8.52 (1H, d, J = 4.8) |
| Id-2 | | C15H15N1 | C, 86.08; H, 7.22; N, 6.69 | C, 85.93; H, 6.78; N, 6.64 | 2.52-2.64 (2H, m), 2.83 (2H, t, J = 7.5), 6.51 (1H, d, J = 15.4), 6.78 (1H, dt, J = 15.8, 6.6), 7.05-7.14 (1H, m), 7.18-7.35 (5H, m), 7.29 (1H, m), 7.59 (1H, dt, J = 1.8, 7.7), 8.52 (1H, d, J = 4.2) |
| Id-4 | 133-140 | C13H11NS-HCl | C, 62.52; H, 4.84; N, 5.61; Cl, 14.19; S, 12.84 | C, 62.48; H, 4.66; N, 5.58; Cl, 14.11; S, 12.81 | 7.19 (1H, d, J = 15.3), 7.31 (1H, d, J = 15.3), 7.33-7.46 (3H, m), 7.48-7.68 (4H, m), 8.04-8.13 (1H, m), 8.67 (1H, dd, J = 2.1 and 6.0) |
| Id-6 | 80-81 | C14H12N2 | C, 80.74; H, 5.81; N, 13.45 | C, 80.52; H, 5.91; N, 13.31 | 7.11 (1H, d, J = 8.8), 7.13-7.30 (2H, m), 7.19 (1H, d, J = 8.8), 7.35-7.46 (3H, m), 7.54-7.59 (2H, m), 7.74 (1H, dt, J = 1.8, 7.7), 8.47 (1H, d, J = 4.6), 9.01 (1H, d, J = 8.2) |

Experiment 1
Activity to Enhance the Expression of Human apoAI

The promoter region of the gene encoding human apoAI was isolated, and ligated upstream the structure gene of firefly luciferase to construct a reporter plasmid. The reporter plasmid and a marker plasmid conferring the neomycin resistance were co-infected to cell lines derived from human hepatoma, HepG2 cells, and the cell lines were incubated in a selection medium comprising DMEM medium containing 10% fetal calf serum supplemented with G418 (Final concentration: 0.7 mg/mL, Gibco) to give established strains that stably expressed the reporter molecule. The strains were seeded to a 96-well culture plates at a density of 50,000 cells per well, and incubated for 48 hours at 37° C. under an atmosphere of 5% carbon dioxide. Then, a solution of the compounds according to the invention in DMSO was added to the wells at final concentrations of 0 to 10 μg/mL. After further incubation for 24 hours, the cells were added with a luciferase assay reagent (Piccagene LT 7.5 registered trade mark, Toyo Ink, KK), and the luciferase activity was determined using a luminometer (MicroBeta™ TRILUX, 1 sec/well, Wallac). The concentration of the compounds, which intensified the luciferase activity twice compared to that of control (DMSO without any compound of the invention added) was set as the minimal effective dose (MED). The results are shown in Table 21.

TABLE 21

| | MED (μg/ml) |
|---|---|
| Ia-1 | 0.53 |
| Ia-3 | 0.12 |
| Ia-6 | 1.5 |
| Ia-13 | 0.5 |
| Ia-14 | 0.41 |
| Ia-15 | 0.57 |
| Ia-16 | 1.6 |
| Ib-1 | 1.1 |
| Ib-9 | 0.71 |
| Ib-50 | 1.2 |
| Ib-56 | 0.13 |

TABLE 21-continued

| | MED (μg/ml) |
|---|---|
| Ib-57 | 0.12 |
| Ib-58 | 0.3 |
| Ib-60 | 0.15 |
| Ib-61 | 0.05 |
| Ib-64 | 0.24 |
| Ib-65 | 0.06 |
| Ib-66 | 0.1 |
| Ib-67 | 0.08 |
| Ib-68 | 0.2 |
| Ib-69 | 0.1 |
| Ib-70 | 0.07 |
| Ib-72 | 0.7 |
| Ib-73 | 1.5 |
| Ib-75 | 0.28 |
| Ib-77 | 1.3 |
| Ib-85 | 0.02 |
| Ib-91 | 0.7 |
| Ic-1 | 0.78 |
| Ic-6 | 0.46 |
| Ic-9 | 0.15 |
| Ic-11 | 0.39 |
| Ic-18 | 1.9 |
| Ic-19 | 1.7 |
| Ic-40 | 0.5 |
| Ic-41 | 0.12 |
| Ic-44 | 0.52 |
| Ic-46 | 0.38 |
| Ic-48 | 0.68 |
| Ic-54 | 0.49 |
| Ic-59 | 1.5 |
| Ic-68 | 0.38 |
| Ic-75 | 1.3 |
| Ic-76 | 0.23 |
| Ic-78 | 0.95 |
| Ic-79 | 1.2 |
| Ic-82 | 1.2 |
| Ic-84 | 1.2 |
| Id-2 | 3.5 |
| Id-4 | 1.0 |

Table 21 shows that the compounds according to the invention can promote the function of the gene encoding human apoAI, thereby enhancing the expression of apoAI.

| Formulation 1 Tablets | |
|---|---|
| compound (I-1) | 15 mg |
| starch | 15 mg |
| lactose | 15 mg |
| crystalline cellulose | 19 mg |
| polyvinyl alcohol | 3 mg |
| distilled water | 30 mL |
| calcium stearate | 3 mg |

The ingredients other than calcium stearate were mixed uniformly, and the mixture was powdered, granulated, and dried to give granules having a suitable size. Then, the calcium stearate was added and the mixture was compressed to give a tablet formulation.

| Formulation 2 Capsules | |
|---|---|
| compound (I-2) | 10 mg |
| magnesium stearate | 10 mg |
| lactose | 80 mg |

The ingredients were homogeneously mixed to give powders or fine particles, which were formed into a powder formulation. This was filled in capsules to give a capsule formulation.

| Formulation 3 Injectable solutions | |
|---|---|
| compound (I-3) | 3 mg |
| gelatin | 150 mg |
| phenol | 4 mg |

The ingredients were dissolved in 1 ml of distilled water for injection. The solution was sterilized by filtration, and filled into vials.

| Formulation 4 Granules | |
|---|---|
| compound (I-4) | 30 g |
| lactose | 265 g |
| magnesium stearate | 5 g |

The ingredients were mixed thoroughly, and the mixture was compressed, powdered, granulated and sieved to give a granule formulation.

INDUSTRIAL APPLICABILITY

As is apparent from the experiment as described above, the compounds according to the invention have an activity for enhancing the expression of apoAI. Thus, the compounds according to the invention are useful as pharmaceutical compositions for preventing and/or treating dyslipidemia or arteriosclerotic diseases, and in a method and use therefor.

The invention claimed is:

1. A method of enhancing the expression of apoAI, which comprises administrating a therapeutically effective amount of a compound of formula (I):

(I)

in which

Ar$^1$ and Ar$^2$ are independently a phenyl that may be optionally substituted, or a naphthyl that may be optionally substituted;

—X— is a group of formula (α):

(α)

wherein
the broken line is the presence or absence of a bond;
-Q= is a group of

 or 

when the broken line is the presence of a bond;
-Q- is —CY²Y³— or —NY⁴— when the broken line is the absence of a bond;
Y² and Y³ are independently a hydrogen, a halogen, a lower alkyl that may be optionally substituted, a carboxy, a lower alkoxycarbonyl that may be optionally substituted, a cyano, a monocyclic carbocyclic group that may be optionally substituted, or a monocyclic heterocyclic group that may be optionally substituted,
Y⁴ is a hydrogen or a lower alkyl;
Z² is a linker group comprising 1 to 2 atoms that combines with the constituent atoms of the ring Ar¹ that are bonded to Z² via the two atoms to form a condensed ring;
provided that, when both Ar¹ and Ar² are a phenyl that may be optionally substituted, then Y² is not a phenyl that may be optionally substituted;
wherein the optional substituent of the phenyl and the naphthyl from the definition of Ar¹ and Ar², and the monocyclic carbocyclic group and the monocyclic heterocyclic group from the definition of Y² and Y³ is selected from the group consisting of a halogen; a hydroxy; a lower alkyl optionally substituted by a halogen, a hydroxy, or a lower alkoxy; a lower alkoxy optionally substituted by a halogen, a hydroxy, a carboxy, or a lower alkoxycarbonyl; a lower alkenyl optionally substituted by a halogen or a hydroxy; a lower alkenyloxy optionally substituted by a halogen or a hydroxy; a lower alkylthio; a non-aromatic carbocyclic group optionally substituted by a halogen, a hydroxy, or a lower alkyl; an acyl; an acyloxy; a carboxy; a lower alkoxycarbonyl; a lower alkenyloxycarbonyl; an amino optionally substituted by a lower alkyl or an acyl; a hydrazino; a nitro; a cyano; a phenyl or naphthyl optionally substituted by a halogen, a hydroxy, a lower alkyl or a lower alkoxy; a heterocyclic group; a phenoxy optionally substituted by a halogen, a hydroxy, or a lower alkyl; a monocyclic aromatic heterocyclic oxy; an oxo; and an alkylenedioxy optionally substituted by a lower alkyl, a lower alkoxy or a phenyl group; and
wherein the optional substituent of the lower alkyl and lower alkoxycarbonyl in the definition of Y² and Y³ is selected from the group consisting of a halogen, a hydroxy, a lower alkoxy, a monocyclic group, a bicyclic carbocyclic group, an acyl, an acyloxy, a carboxy, a lower alkoxycarbonyl, an amino, a lower alkylamino, a nitro, a monocyclic group and a bicyclic heterocyclic group;
or a pharmaceutically acceptable salt thereof to a patient expected to enhance the expression of apoAI.

2. The method according to claim 1, in which the broken line is the presence of a bond.

3. The method according to claim 1, in which -Q= is a group of

4. The method of claim 3, in which Y² is hydrogen.

5. The method according to claim 1, in which -Q= is a group of

6. The method according to claim 2, in which -Q= is a group of

7. The method according to claim 1, 2, 3, 4, 5 or 6, in which Z² is a linker group comprising 2 atoms that combines with the constituent atoms of the ring Ar¹ that are bonded to Z² via the two atoms to form a condensed ring.

8. The method according to claim 1,
wherein X is

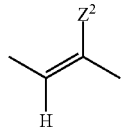

and
Z² is a linker group comprising 2 atoms that combines with the constituent atoms of the ring Ar¹ that are bonded to Z² via the two atoms to form a condensed ring.

9. The method according to claim 1,
wherein X is

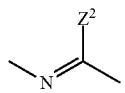

and
Z² is a linker group comprising 2 atoms that combines with the constituent atoms of the ring Ar¹ that are bonded to Z² via the two atoms to form a condensed ring.

* * * * *